United States Patent
Yamaji

(10) Patent No.: US 11,051,753 B2
(45) Date of Patent: Jul. 6, 2021

(54) INFORMATION PROCESSING METHOD AND INFORMATION PROCESSING APPARATUS

(71) Applicant: FUJITSU LIMITED, Kawasaki (JP)

(72) Inventor: Takayuki Yamaji, Yokohama (JP)

(73) Assignee: FUJITSU LIMITED, Kawasaki (JP)

( * ) Notice: Subject to any disclaimer, the term of this patent is extended or adjusted under 35 U.S.C. 154(b) by 103 days.

(21) Appl. No.: 16/516,271

(22) Filed: Jul. 19, 2019

(65) Prior Publication Data

US 2019/0336067 A1 Nov. 7, 2019

Related U.S. Application Data

(63) Continuation of application No. PCT/JP2017/003916, filed on Feb. 3, 2017.

(51) Int. Cl.
*A61B 5/00* (2006.01)
*G16H 50/30* (2018.01)
(Continued)

(52) U.S. Cl.
CPC .......... *A61B 5/4815* (2013.01); *A61B 5/1118* (2013.01); *A61B 5/4809* (2013.01); *A61B 5/743* (2013.01); *G06T 11/60* (2013.01); *G16H 30/40* (2018.01); *G16H 50/30* (2018.01); *A61B 2562/0219* (2013.01)

(58) Field of Classification Search
CPC ... A61B 5/4815; A61B 5/1118; A61B 5/4809; A61B 5/743; A61B 2562/0219; A61B 5/0816; A61B 5/024; A61B 5/681; A61B 5/0002; G16H 50/30; G16H 30/40; G16H 50/20; G16H 40/63; G16H 20/30; G06T 11/60; G06T 11/206

See application file for complete search history.

(56) References Cited

U.S. PATENT DOCUMENTS

2006/0094938 A1 5/2006 Shimada et al.
2008/0004811 A1 1/2008 Suzuki et al.
(Continued)

FOREIGN PATENT DOCUMENTS

JP 2006-129887 A 5/2006
JP 2008-006005 A 1/2008
(Continued)

OTHER PUBLICATIONS

Patel SR, Weng J, Rueschman M et al.Reproducibility of a standardized actigraphy scoring algorithm for sleep in a US Hispanic/Latino population. Sleep; 2015;389: pp. 1497-1503 (Year: 2015).*
(Continued)

*Primary Examiner* — Kyle Zhai
*Assistant Examiner* — Andrew Shin
(74) *Attorney, Agent, or Firm* — Xsensus LLP

(57) ABSTRACT

Disclosed is an information processing method executed by a computer. The information processing method includes identifying a sleep onset time and an awakening time based on time series data relating to an activity status of a user; calculating a first midpoint at which an interval between the sleep onset time and the awakening time is evenly divided into two; and outputting information indicating a time at the calculated first midpoint.

9 Claims, 37 Drawing Sheets

(51) Int. Cl.
  *G16H 30/40* (2018.01)
  *A61B 5/11* (2006.01)
  *G06T 11/60* (2006.01)

(56) References Cited

U.S. PATENT DOCUMENTS

| | | | | |
|---|---|---|---|---|
| 2011/0267196 | A1* | 11/2011 | Hu | A61B 5/681 340/575 |
| 2012/0143095 | A1 | 6/2012 | Nakamura | |
| 2017/0251986 | A1 | 9/2017 | Yamaji | |

FOREIGN PATENT DOCUMENTS

| | | |
|---|---|---|
| JP | 2011-067241 A | 4/2011 |
| JP | 2013-168026 A | 8/2013 |
| JP | 2015-171555 A | 10/2015 |
| WO | 2011/027651 A1 | 3/2011 |
| WO | 2016/067449 A1 | 5/2016 |

OTHER PUBLICATIONS

Simpkin CT, Jenni OG, Carskadon MA, et al. Chronotype is associated with the timing of the circadian clock and sleep in toddlers. J Sleep Res. 2014;23: pp. 397-405 (Year: 2014).*

Koscec A, Radosevic-Vidacek B, Bakotic M. (2014). Morningness-eveningness and sleep patterns of adolescents attending school in two rotating shifts. Chronobiol Int. 31: pp. 52-63 (Year: 2014).*

S. Warner, G. Murray, D. Meyer. Holiday and school-term sleep patterns of Australian adolescents. J Adolesc, 31 (2008), pp. 595-608 (Year: 2008).*

International Search Report and Written Opinion dated Apr. 4, 2017 for PCT/JP2017/003916 filed on Feb. 3, 2017, 12 pages including English Translation of the International Search Report and Written Opinion.

Till Roenneberg, "Light and the Human Circadian Clock", Handbook of experimental pharmacology / Apr. 2013 [online], 2014, p. 311 to 331, DOI: 10.1007/978-3 to 642, and to 25950, and to 0_13,URL, https://www.researchgate. net/publication/236253090_Light_and_the_Human_Circadian_Clock.

Helene Werner, "Assessment of Chronotype in Four-to Eleven-Old Children: Reliability and Validity of the Children's ChronoType Questionnaire (CCTQ)", Chronobiology International, The Journal of Biological and Medical Rhythm Research [online], 2010, p. 992-1014,doi: 10.1080/07420520903044505, URL, https://www.tandfonline.com/doi/full/10.1080/0742052090 3044505.

Till Roenneberg, "Life between Clocks: Daily Temporal Patterns of Human Chronotypes", Journal of Biological Rhythms [online], 2003, vol. 18 No. 1,p. 80 / 90,doi: 10.1177/0748730402239679,URL https://pubmed.ncbi.nlm.nih.gov/12568247.

Japanese Office Action dated Nov. 4, 2020, in corresponding Japanese Patent Application No. 2018-565190.

* cited by examiner

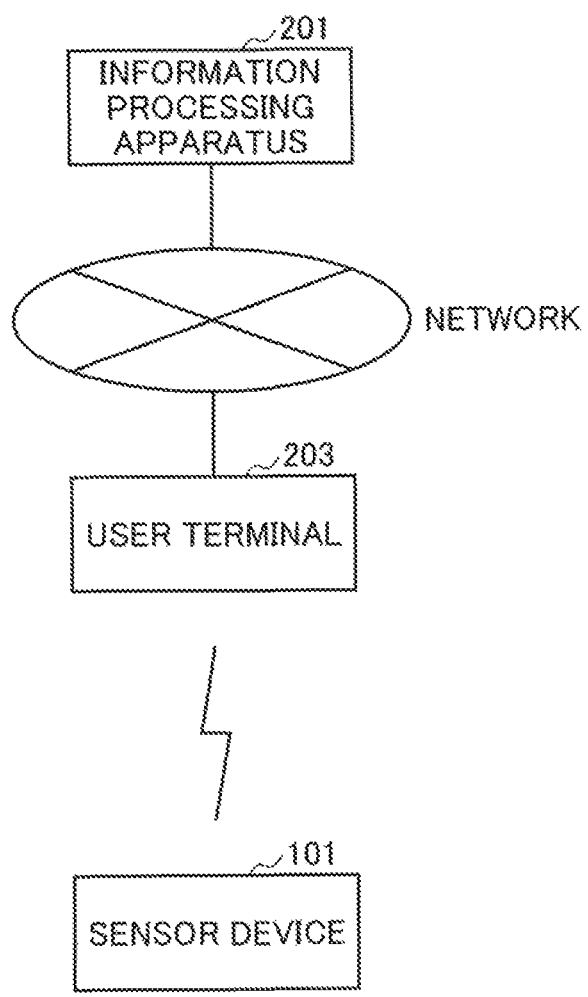

FIG.5

| DATE AND TIME | ACCEL-ERATION | ACTIVITY AMOUNT | BODY POSITION | EVENT | USER'S STATUS |
|---|---|---|---|---|---|
| ⋮ | ⋮ | ⋮ | ⋮ | ⋮ | ⋮ |
| JAN-10-2017 12:00 | A10_360 | B10_360 | STANDING POSITION | NONE | AWAKE STATUS |
| JAN-10-2017 12:02 | A10_361 | B10_361 | STANDING POSITION | NONE | AWAKE STATUS |
| JAN-10-2017 12:04 | A10_362 | B10_362 | STANDING POSITION | NONE | AWAKE STATUS |
| ⋮ | ⋮ | ⋮ | ⋮ | ⋮ | ⋮ |
| JAN-10-2017 22:28 | A10_674 | B10_674 | PRONE POSITION | NONE | AWAKE STATUS |
| JAN-10-2017 22:30 | A10_675 | B10_675 | SUPINE POSITION | NONE | AWAKE STATUS |
| JAN-10-2017 22:32 | A10_676 | B10_676 | SUPINE POSITION | NONE | AWAKE STATUS |
| ⋮ | ⋮ | ⋮ | ⋮ | ⋮ | ⋮ |
| JAN-10-2017 22:48 | A10_684 | B10_684 | SUPINE POSITION | NONE | AWAKE STATUS |
| JAN-10-2017 22:50 | A10_685 | B10_685 | SUPINE POSITION | SLEEP ONSET | SLEEP STATUS |
| JAN-10-2017 22:52 | A10_686 | B10_686 | SUPINE POSITION | NONE | SLEEP STATUS |
| ⋮ | ⋮ | ⋮ | ⋮ | ⋮ | ⋮ |
| JAN-11-2017 5:48 | A11_174 | B11_174 | LATERAL POSITION | NONE | SLEEP STATUS |
| JAN-11-2017 5:50 | A11_175 | B11_175 | SUPINE POSITION | AWAK-ENING | AWAKE STATUS |
| JAN-11-2017 5:52 | A11_176 | B11_176 | SUPINE POSITION | NONE | AWAKE STATUS |
| ⋮ | ⋮ | ⋮ | ⋮ | ⋮ | ⋮ |
| JAN-11-2017 6:28 | A11_194 | B11_194 | SUPINE POSITION | NONE | AWAKE STATUS |
| JAN-11-2017 6:30 | A11_195 | B11_195 | PRONE POSITION | NONE | AWAKE STATUS |
| JAN-11-2017 6:32 | A11_196 | B11_196 | STANDING POSITION | NONE | AWAKE STATUS |
| ⋮ | ⋮ | ⋮ | ⋮ | ⋮ | ⋮ |

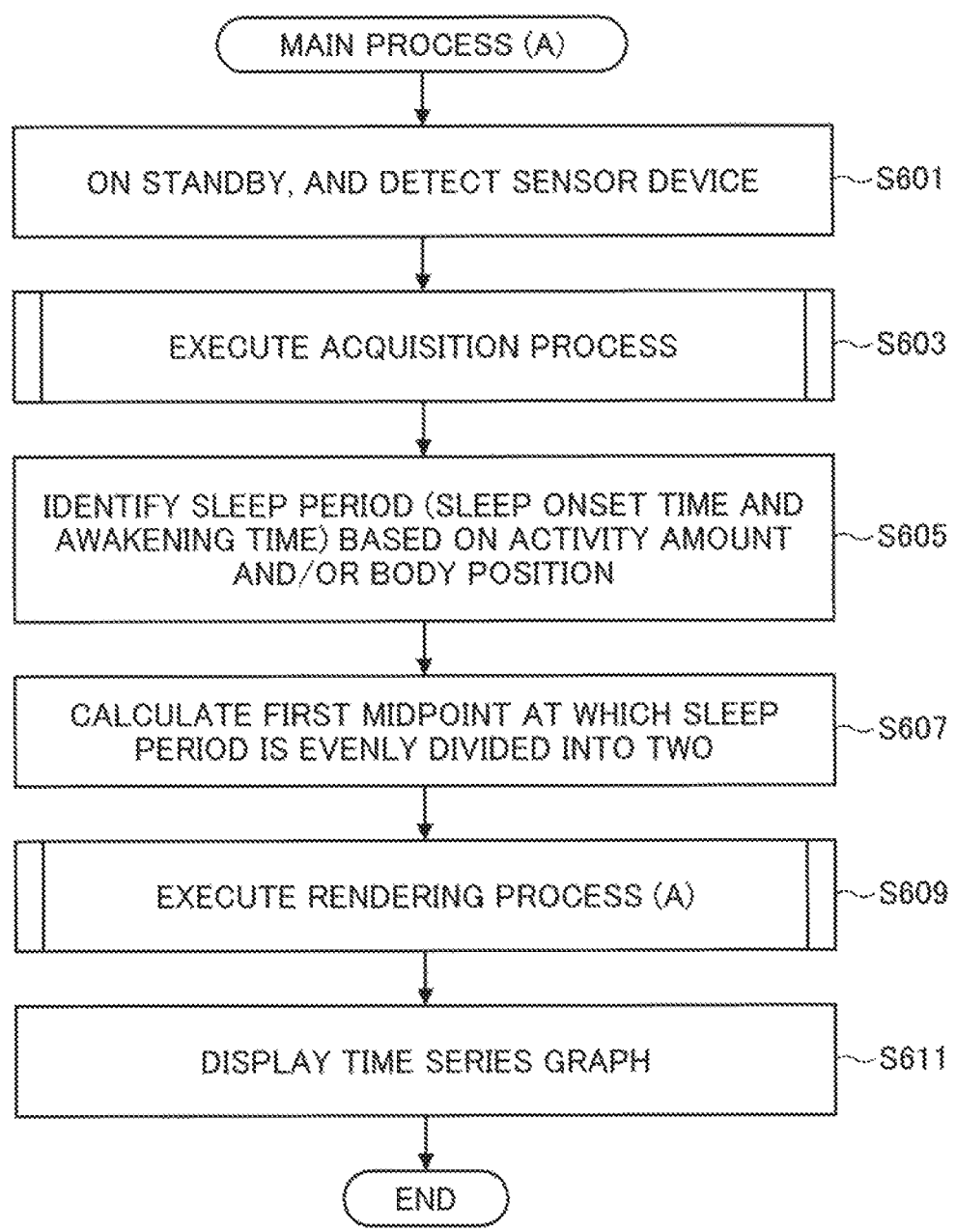

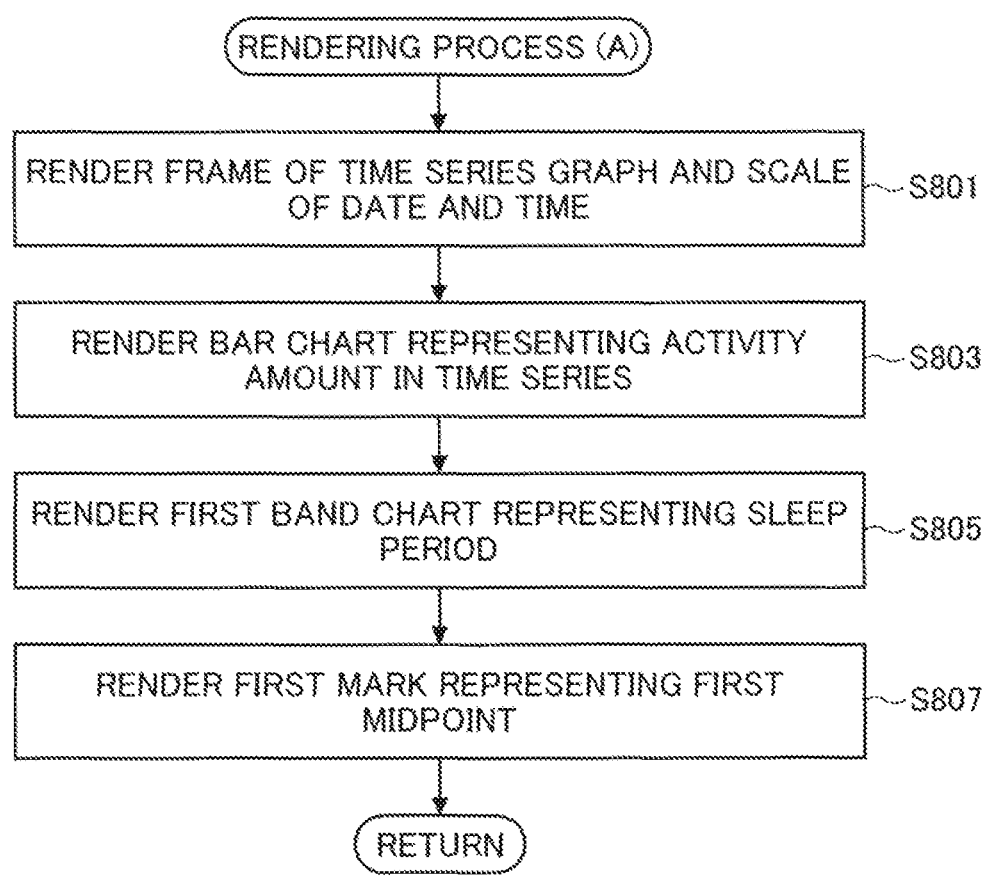

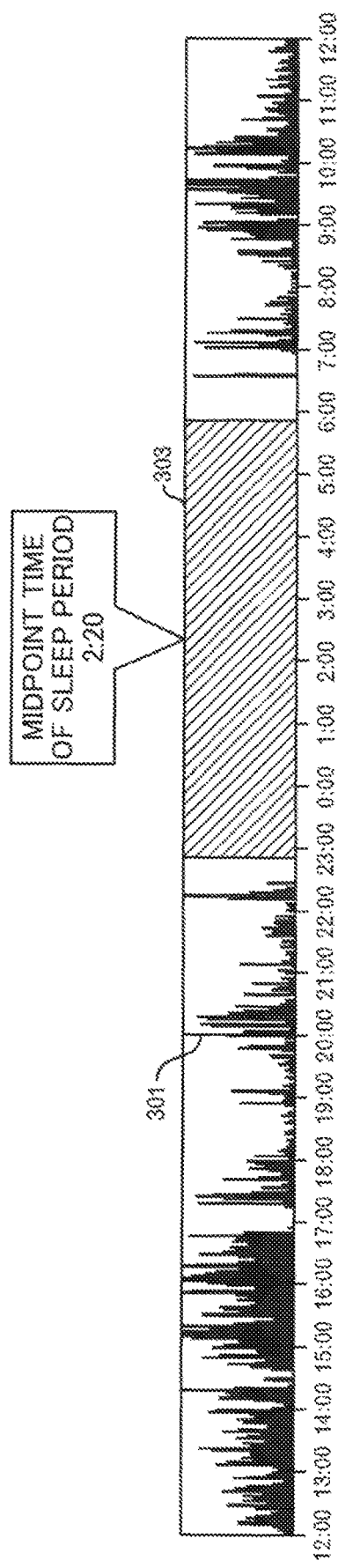

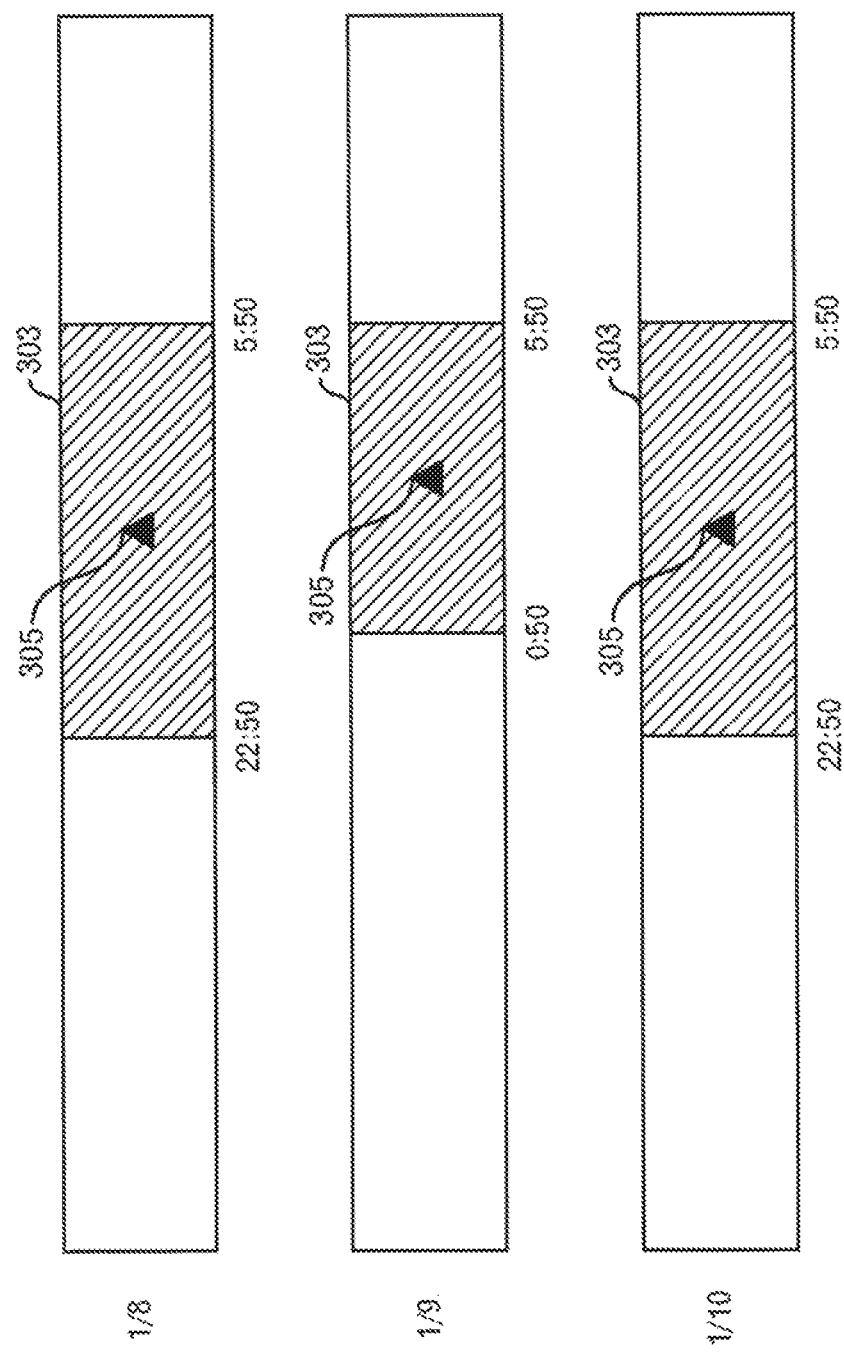

FIG.12

| DATE | PERIOD COVERED | HOLIDAY/WORKING DAY DISTINCTION | WORKING ARRANGEMENT |
|---|---|---|---|
| ... | ... | ... | ... |
| JAN-10 | JAN-10 12:00 TO IMMEDIATELY BEFORE JAN-11 12:00 | WORKING DAY | DAYTIME SHIFT |
| JAN-11 | JAN-11 12:00 TO IMMEDIATELY BEFORE JAN-12 12:00 | WORKING DAY | DAYTIME SHIFT |
| JAN-12 | JAN-12 12:00 TO IMMEDIATELY BEFORE JAN-13 12:00 | WORKING DAY | DAYTIME SHIFT |
| JAN-13 | JAN-13 12:00 TO IMMEDIATELY BEFORE JAN-14 12:00 | HOLIDAY | - |
| JAN-14 | JAN-14 12:00 TO IMMEDIATELY BEFORE JAN-15 12:00 | WORKING DAY | NIGHTTIME SHIFT |
| ... | ... | ... | ... |

FIG.15

| DATE AND TIME | ACCEL-ERATION | ACTIVITY AMOUNT | BODY POSITION | EVENT | USER'S STATUS |
|---|---|---|---|---|---|
| ⋮ | ⋮ | ⋮ | ⋮ | ⋮ | ⋮ |
| JAN-10-2017 12:00 | A10_360 | B10_360 | STANDING POSITION | NONE | AWAKE STATUS |
| JAN-10-2017 12:02 | A10_361 | B10_361 | STANDING POSITION | NONE | AWAKE STATUS |
| JAN-10-2017 12:04 | A10_362 | B10_362 | STANDING POSITION | NONE | AWAKE STATUS |
| ⋮ | ⋮ | ⋮ | ⋮ | ⋮ | ⋮ |
| JAN-10-2017 22:28 | A10_674 | B10_674 | PRONE POSITION | NONE | AWAKE STATUS |
| JAN-10-2017 22:30 | A10_675 | B10_675 | SUPINE POSITION | GETTING INTO BED | AWAKE STATUS |
| JAN-10-2017 22:32 | A10_676 | B10_676 | SUPINE POSITION | NONE | AWAKE STATUS |
| ⋮ | ⋮ | ⋮ | ⋮ | ⋮ | ⋮ |
| JAN-10-2017 22:48 | A10_684 | B10_684 | SUPINE POSITION | NONE | AWAKE STATUS |
| JAN-10-2017 22:50 | A10_685 | B10_685 | SUPINE POSITION | SLEEP ONSET | SLEEP STATUS |
| JAN-10-2017 22:52 | A10_686 | B10_686 | SUPINE POSITION | NONE | SLEEP STATUS |
| ⋮ | ⋮ | ⋮ | ⋮ | ⋮ | ⋮ |
| JAN-11-2017 5:48 | A11_174 | B11_174 | LATERAL POSITION | NONE | SLEEP STATUS |
| JAN-11-2017 5:50 | A11_175 | B11_175 | SUPINE POSITION | AWAK-ENING | AWAKE STATUS |
| JAN-11-2017 5:52 | A11_176 | B11_176 | SUPINE POSITION | NONE | AWAKE STATUS |
| ⋮ | ⋮ | ⋮ | ⋮ | ⋮ | ⋮ |
| JAN-11-2017 6:28 | A11_194 | B11_194 | SUPINE POSITION | NONE | AWAKE STATUS |
| JAN-11-2017 6:30 | A11_195 | B11_195 | PRONE POSITION | GETTING OUT OF BED | AWAKE STATUS |
| JAN-11-2017 6:32 | A11_196 | B11_196 | STANDING POSITION | NONE | AWAKE STATUS |
| ⋮ | ⋮ | ⋮ | ⋮ | ⋮ | ⋮ |

INFORMATION PROCESSING METHOD AND INFORMATION PROCESSING APPARATUS

CROSS-REFERENCE TO RELATED APPLICATIONS

This application is a continuation application of International Application PCT/JP2017/003916 filed on Feb. 3, 2017 and designated the U.S., the entire contents of which are incorporated herein by reference.

FIELD

The disclosures discussed herein relate to a technology for providing information based on sleep data.

BACKGROUND

A system for detecting a user's sleep period is beginning to be utilized through measurement data of a sensor worn by a user. For example, in a company where many employees work every day, the company collects information about each employee's sleep and use it for health management.

However, an appropriate sleep period depends on the individual. Further, a sleep period may be temporarily restricted according to some occupations.

Thus, it may not be possible to assess sleep correctly by simply setting standards for sleep length. In addition, even if attention is paid to a sleep onset time (i.e., time of falling asleep) and an awakening time, correct evaluation may not be achieved.

It may be required to provide information useful in evaluating sleep, taking into account individual difference and working conditions.

RELATED ART DOCUMENT

Patent Document

Patent Document 1: Japanese Laid-open Patent Publication No. 2006-129887
Patent Document 2: Japanese Laid-open Patent Publication No. 2008-6005

SUMMARY

In one aspect of embodiments, it is desirable to output information about a midpoint time of a sleep period.

According to one aspect of embodiments, an information processing method executed by a computer is disclosed. The information processing method includes (A) identifying a sleep onset time and an awakening time based on time series data relating to an activity status of a user;

(B) calculating a first midpoint at which an interval between the sleep onset time and the awakening time is evenly divided into two; and (C) outputting information indicating the time at the calculated first midpoint.

The above-described respective units may be a computer-readable recording medium having stored therein a method or a program for causing a computer to execute processing of the respective units.

The above-described respective units may be a computer-readable recording medium having stored therein a method or a program for causing a computer to execute processing of the respective units.

The object and advantages of the embodiment will be realized and attained by means of the elements and combinations particularly pointed out in the claims. It is to be understood that both the foregoing general description and the following detailed description are exemplary and explanatory and are not restrictive of the invention, as claimed.

BRIEF DESCRIPTION OF DRAWINGS

FIG. 2B is a diagram illustrating an example of a connection configuration:

FIG. 5 is a diagram illustrating an example of a first table;

FIG. 6 is a diagram illustrating a flowchart of a main process (A):

FIG. 8 is a diagram illustrating a flowchart of a rendering process (A);

FIG. 9 is a diagram illustrating an example of a time series graph;

FIG. 10B is a diagram illustrating an example of a set of time series graphs according to the second embodiment;

FIG. 12 is a diagram illustrating an example of a second table:

FIG. 15 is a diagram illustrating an example of a first table according to the third embodiment;

DESCRIPTION OF EMBODIMENTS

In the following, embodiments of the present invention will be described with reference to the accompanying drawings.

First Embodiment

Figure 1:
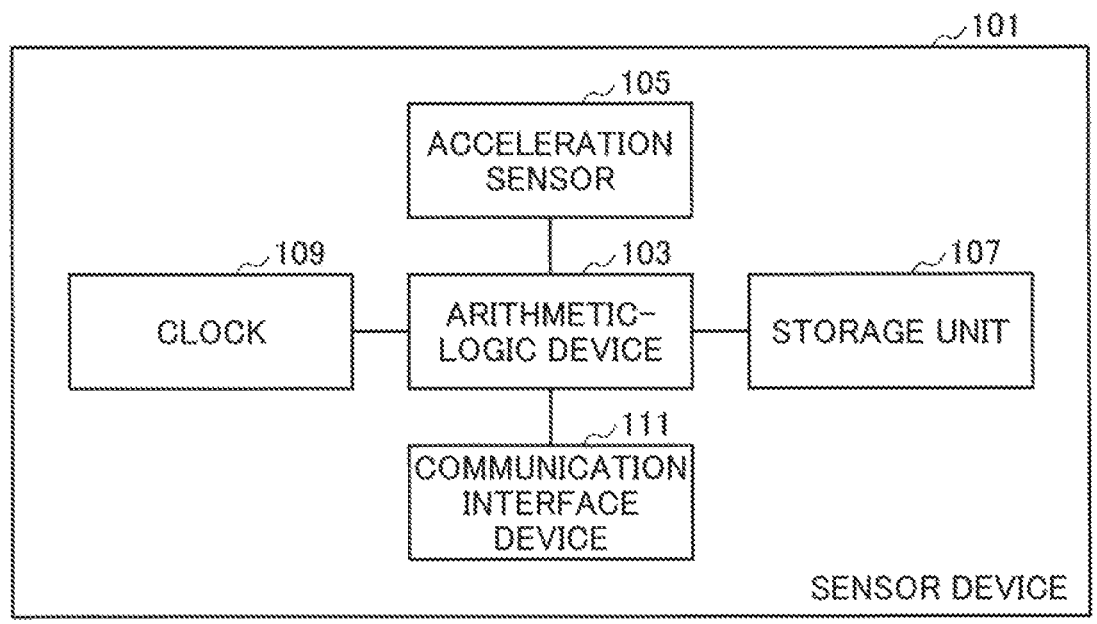
FIG. 1 is a diagram illustrating an example of a hardware configuration of a sensor device.

FIG. 1 illustrates an example of a hardware configuration of a sensor device 101. While a user wears the sensor device 101, the sensor device 101 measures acceleration. For example, the sensor device 101 is attached to a belt or pants such that the sensor device 101 is attached to a position of the user's waist. However, the sensor device 101 may be attached to other parts of the user's body parts (e.g., head, neck, chest, abdomen, back, arm or foot). Alternatively, instead of the sensor device 101 illustrated in FIG. 1, a wearable terminal or a mobile phone terminal may be used.

The sensor device 101 includes an arithmetic-logic device 103, an acceleration sensor 105, a storage unit 107, a clock 109, and a communication interface device 111. The arithmetic-logic device 103 performs various types of arithmetic-logic processes. The acceleration sensor 105 measures acceleration. The storage unit 107 stores various types of data and programs. The clock 109 measures a date and time. The communication interface device 111 is, for example, a wireless IC (Integrated Circuit) tag or a USB (Universal Serial Bus) interface. The communication interface device 111 may be any other near-range radio interface device.

The sensor device 101 stores acceleration data with a measurement date and time, i.e., acceleration time series data. Then, the acceleration time series data is output through the communication interface device 111.

The sensor device 101 may also calculate the amount of activity of a user based on the acceleration time series data. Then, the sensor device 101 may output the time series data of the calculated activity amount through the communication interface device 111. The method for calculating the amount of activity is according to the related art.

The sensor device 101 may also determine body positions of a user based on acceleration time series data. Then, the sensor device 101 may output time series data of the determined body positions through the communication interface device 111. The method for determining body positions is according to the related art. The sensor device 101 may be a sensor other than the acceleration sensor 105 if such a sensor is capable of measuring a sleep status of a user. Examples include an electromagnetic wave sensor capable of detecting movement of the body such as the heart or lungs, a sensor capable of detecting pulse or breathing, and an electromagnetic wave sensor or an image sensor capable of detecting movements of the body itself. In this case, the sensor device 101 may store time series data for all of or some of the heart rate, respiratory rate, and body movements, and output the stored time series data through the communication interface device 111. Alternatively, the measured data may be output through the communication interface device 111, and all of or some of the heart rate, respiratory rate, and body movements may be detected by another computer and stored as time series data.

A user wearing the sensor device 101 (i.e., a subject of sleep evaluation) is, for example, a railway or vehicle driver. In this example, a manager of such drivers is expected to identify the quality of sleep of drivers who are to be engaged in driving operations to ensure driving operation safety.

Figure 2A:
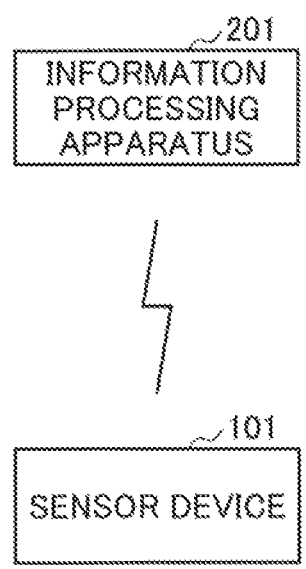
FIG. 2A is a diagram illustrating an example of a connection configuration.

Hence, the information processing apparatus used by the manager reads and analyzes the data stored in the sensor device 101. FIG. 2A illustrates an example of a connection configuration. In this example, an information processing apparatus 201 directly reads data from the sensor device 101. For example, when a driver is at a place of work with his/her manager, the information processing apparatus 201 directly reads data from the sensor device 101, which results in less time-consuming work. Before the departure of an outward journey from a place of work to the destination, such a connection configuration may be used.

In the case of a return journey from the destination to the place of work, a connection configuration as illustrated in FIG. 2B may be used. First, the user terminal 203 reads data stored in the sensor device 101. The user terminal 203 transfer the data read to the information processing apparatus 201. The user terminal 203 thus includes a reader compatible with the communication interface device 111 of the sensor device 101 so as to transmit data through a network. The network may be, for example, the Internet, a dedicated line, or a local area network (LAN). The user terminal 203 is, for example, a tablet terminal or a node book PC. The user terminal 203 may be a mobile phone terminal such as a smartphone. In FIG. 2B, an example of connection configuration for the user terminal 203 and the information processing apparatus 201 being separate devises is illustrated, but the connection configuration is not required to be such a connection configuration for separate entities. For example, the connection configuration for a module of the information processing apparatus 201 being implemented in the user terminal 203 may be used.

In addition to a driver, a user, such as an operator of the machine, a supervisor, or a health care professional, may use the sensor device 101.

Figure 3:
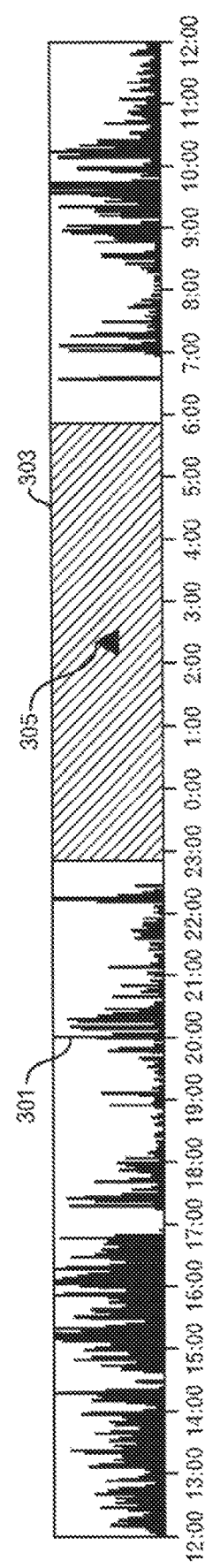
FIG. 3 is a diagram illustrating an example of a time series graph.

A time series graph presented in this embodiment will be described with reference to FIG. 3. The amount of activity from a predetermined start time to a predetermined end time is represented by a bar chart 301. In addition, a sleep period during that period of the predetermined start time to the predetermined end time of activity is represented by a first band chart 303. A first mark 305 indicates a time at the midpoint (hereinafter called "midpoint time") of a sleep period. The midpoint time is a representative time point of the sleep period.

Figure 4:
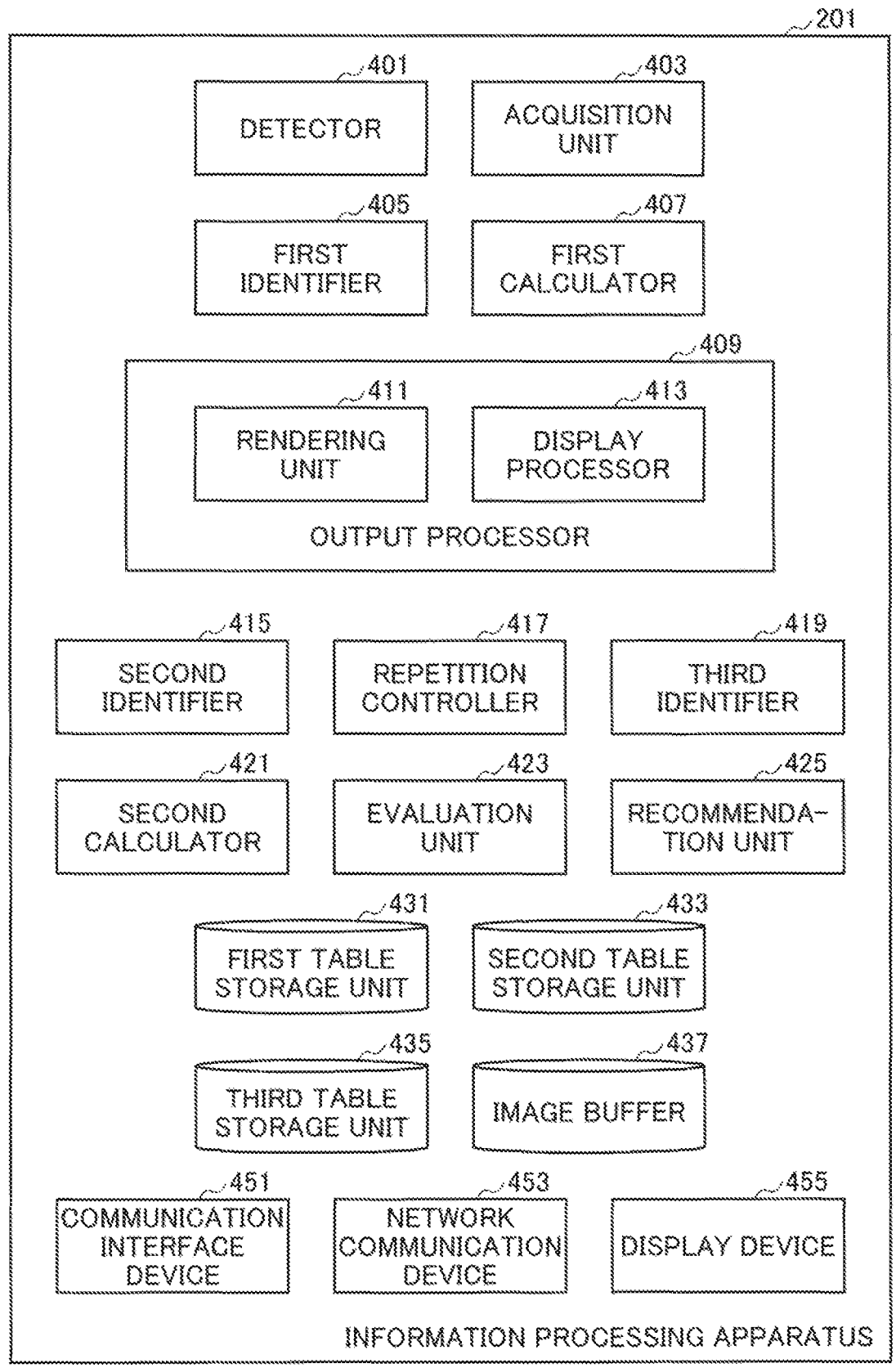
FIG. 4 is a diagram illustrating an example of a module configuration of an information processing apparatus.

Next, operation of the information processing apparatus 201 will be described. FIG. 4 illustrates an example of a module configuration of the information processing apparatus 201. The information processing apparatus 201 includes a detector 401, an acquisition unit 403, a first identifier 405, a first calculator 407, an output processor 409, a second identifier 415, a repetition controller 417, a third identifier 419, a second calculator 421, an evaluation unit 423, a recommendation unit 425, a first table storage unit 431, a second table storage unit 433, a third table storage unit 435, an image buffer 437, a communication interface device 451, a network communication device 453, and a display device 455.

The detector 401 detects the sensor device 101. The acquisition unit 403 acquires time series data used for analysis from the sensor device 101. The first identifier 405 identifies a sleep period (a sleep onset time and an awakening time), based on time series data of the activity amount and/or time series data of body positions. The first calculator 407 calculates a first midpoint at which the sleep period is evenly divided into two.

The output processor 409 outputs various types of data. In this example, the output processor 409 includes a rendering unit 411 and a display processor 413. The rendering unit 411 renders, for example, a time series graph or a comment. The display processor 413 displays a rendered image on the display device 455. The output form of a rendered result may be, for example, printing, writing to a storage medium, or transmission.

The second identifier 415 identifies a date to be displayed. The repetition controller 417 controls a repetition process in a main process. The third identifier 419 identifies a stay-in-bed period, which indicates a time while a user stays in bed (i.e., an interval between a time of getting into bed and a time of getting out of bed), based on time series data of the activity amount and/or time series data of body positions. The second calculator 421 calculates a second midpoint at which the stay-in-bed period is divided equally into two.

An evaluation unit 423 evaluates the quality of sleep. The evaluation unit 423 will be described later with reference to FIG. 21. A recommendation unit 425 presents various recommendation times as a guide for sleep. The recommendation unit 425 will be described later with reference to FIG. 31.

The first table storage unit 431 stores a first table. The first table will be described later with reference to FIGS. 5 and 15. The second table storage unit 433 stores a second table. The second table will be described later with reference to FIG. 12. The third table storage unit 435 stores a third table. The third table swill be described later with reference to FIG. 22. The image buffer 437 stores images of rendered time series graphs and comments.

The above-described detector 401, acquisition unit 403, first identifier 405, first calculator 407, output processor 409, rendering unit 411, display processor 413, second identifier 415, repetition controller 417, third identifier 419, second calculator 421, evaluation unit 423, and recommendation unit 425 are implemented using hardware resources (e.g., FIG. 35) and a program that causes processors to execute a process described below.

Figure 35:
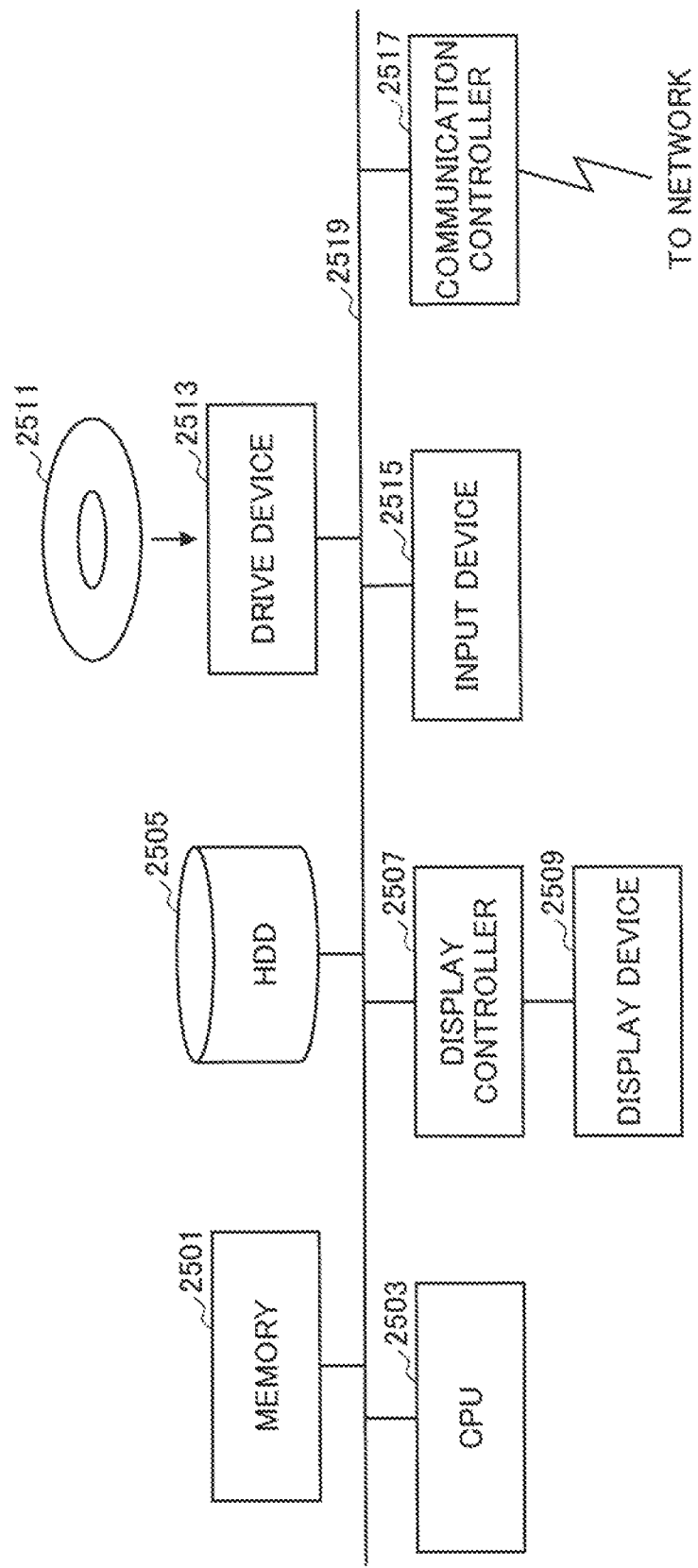
FIG. 35 is a functional block diagram of a computer.

The first table storage unit 431, the second table storage unit 433, the third table storage unit 435, and the image buffer 437 described above are implemented using hardware resources (e.g., FIG. 35).

The communication interface device 451 communicates with the communication interface device 111 of the sensor device 101. The communication interface device 451 is, for example, a reader or USB interface of a wireless IC tag. The communication interface device 451 may be any other near-range radio interface device. The network communication device 453 communicates through a network. A display device 455 displays, for example, a time series graph or comment by a display process. The display device 455 has a normal function of displaying an image and may be a general purpose device.

FIG. 5 illustrates an example of the first table. The first table in this example has records each corresponding to an acceleration measuring time. Each record of the first table includes a field in which a date and time is stored, a field in which an acceleration is stored, a field in which an activity amount is stored, a field in which a body position is stored, a field in which an event is stored, and a field in which a user's status is stored.

The date and time specifies a timing at which the acceleration is measured. Body positions include, for example, the prone, supine, lateral, and standing positions. Events are either sleep onset (i.e., falling asleep) or awakening. The user's status is either an awake status or a sleep status. The sleep onset indicates the user's status being switched from an awake status to a sleep status. The awakening indicates the user's status being switched from the sleep status to awake status.

The following illustrates processes executed in the information processing apparatus 201. FIG. 6 illustrates a flowchart of a main process (A). The detector 401 is on standby and detects a sensor device 101 (S601). Specifically, the communication interface device 451 of the information processing apparatus 201 communicates with the communication interface device 111 of the sensor device 101.

Upon the sensor device 101 being detected by the detector 401, the acquisition unit 403 executes an acquisition process (S603). In the acquisition process, the acquisition unit 403 acquires time series data for use in an analysis from the sensor device 101. In this example, it is assumed that the acquisition unit 403 is operated to acquire data for one day.

Figure 7A:
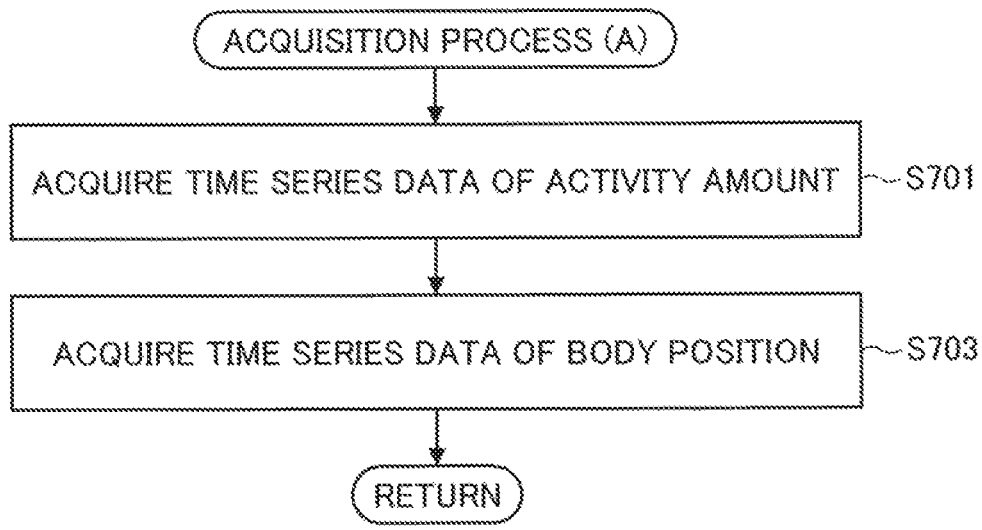
FIG. 7A is a diagram illustrating a flowchart of an acquisition process (A)

FIG. 7A illustrates a flowchart of the acquisition process (A).

In the acquisition process (A), it is assumed that the sensor device 101 calculates the activity amount and further determines a body position.

The acquisition unit 403 acquires time series data of the activity amount by the communication interface device 451 (S701).

The acquisition unit 403 further acquires time series data of body positions by the communication interface device 451 (S703).

When the acquisition process (A) ends, the process returns to the invoking source main process (A).

To perform analysis based on the time series data of the activity amount alone, the acquisition unit 403 may be configured not to acquire the time series data of body positions.

To perform analysis based on the time series data of body positions alone, the acquisition unit 403 may be configured not to acquire the time series data of the activity amount.

Figure 7B:
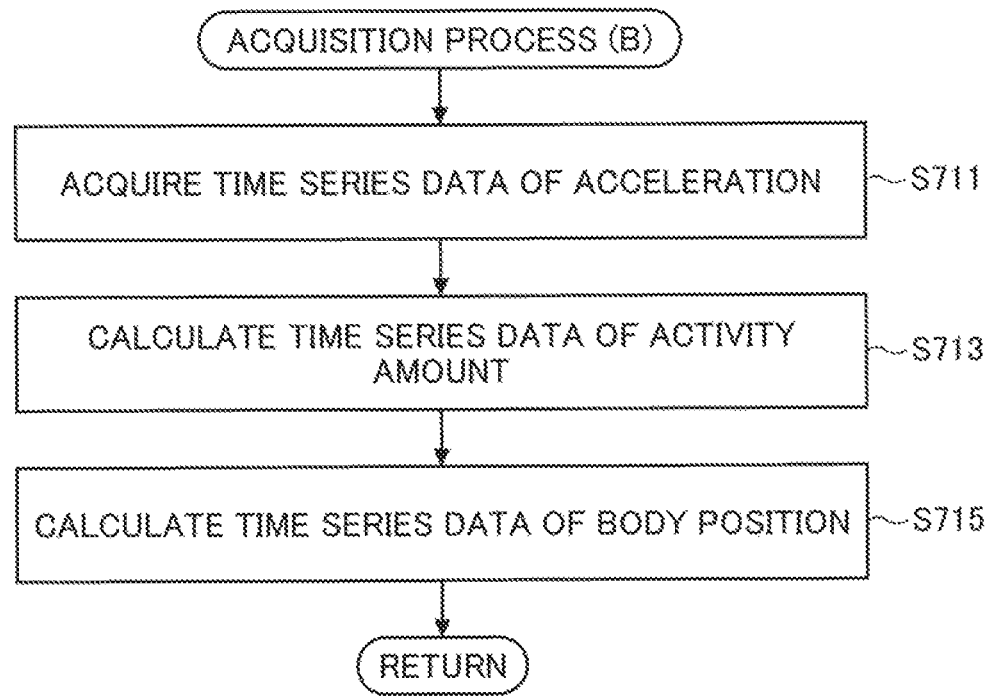
FIG. 7B is a diagram illustrating a flowchart of an acquisition process (B)

The acquisition unit 403 may execute an acquisition process (B) illustrated in FIG. 7B instead of the acquisition process (A). In the acquisition process (B), the acquisition unit 403 acquires only the acceleration time series data. Accordingly, the sensor device 101 may not calculate the amount of activity. Further, the sensor device 101 may not determine a body position.

The acquisition unit 403 acquires acceleration time series data by the communication interface device 451 (S711). The acquisition unit 403 calculates the time series data of the activity amount based on the acceleration time series data (S713). The method for calculating the amount of activity is according to the related art. Further, the acquisition unit 403 calculates time series data of body positions based on the time series data of acceleration (S715). The method for determining a body position is according to the related art.

To perform analysis based on the time series data of the activity amount alone, the acquisition unit 403 may be configured not to compute the time series data of body positions. To perform analysis based on the time series data of body positions alone, the acquisition unit 403 may be configured not to calculate the time series data of the activity amount. When the acquisition process (B) ends, the process returns to the invoking source main process (A).

In this example, the communication interface device 451 is configured to acquire time series data; however, the network communication device 453 may be configured to receive time series data instead. Data acquired by the acquisition process (A) or the acquisition process (B) is stored in the first table.

The following description is given by referring back to FIG. 6. The first identifier 405 identifies the sleep period (a sleep onset time and an awakening time), based on time series data of the activity amount and/or time series data of body positions (S605). A method for identifying a sleep onset time and an awakening time are according to the related art. A code indicating sleep onset and a code indicating awakening are both then stored in the event fields of the current record in the first table. As described above, when a sensor other than the acceleration sensor 105 is used, the first identifier 405 may identify the sleep onset time and the awakening time, from all of or some of the time series data of the heart rate, respiratory rate, and the body movements.

The first calculator 407 calculates a first midpoint at which the sleep period is evenly divided into two (S607). Specifically, a time (time point) at the first midpoint is obtained by adding a time (time interval) equivalent to half the length of the sleep period to the sleep onset time (time point). Alternatively, a time (time point) at the first midpoint may be obtained by subtracting a time (time interval) equivalent to half the length of the sleep period from the awakening time (time point).

The rendering unit 411 executes a rendering process (A) (S609). In the rendering process (A), a time series graph illustrated in FIG. 3 is rendered.

FIG. 8 illustrates a flowchart of a rendering process (A). The rendering unit 411 first renders a frame of a time series graph and a date and time scale (S801). The rendering unit 411 renders a bar chart 301 representing the amount of activity in time series within a display period (S803). The rendering unit 411 renders a first band chart 303 representing a sleep period included in the display period (S805). The rendering unit 411 then renders a first mark 305 representing a first midpoint at a position corresponding to the first midpoint (S807). The rendered images of the frame, date and time scale, bar chart 301, first band chart 303, and first mark 305 are stored in image buffer 437. When the rendering process (A) ends, the process returns to the invoking source main process (A).

The following description is given by referring back to FIG. 6. In S611, the display processor 413 displays a time series graph. Specifically, the display device 455 displays images of the frame, date and time, bar chart 301, first band chart 303, and first mark 305 rendered by the display processor 413 in the rendering process (A). Then, the main process (A) ends. Note that the output form of the time series graph is not limited to display. The output processor 409 may print a time series graph. The output processor 409 may write a time series graph to a storage medium. Alternatively, the output processor 409 may transmit a time series graph. The same applies to a main process illustrated below.

In the example described above, the rendering unit 411 renders a first mark 305 at a position corresponding to the first midpoint. However, other display elements such as lines may be rendered and displayed. Further, as illustrated in FIG. 9, the output processor 409 may display a time at the first midpoint in a balloon, for example, with numerals or other symbols (or numerals and characters).

According to the first embodiment, it is easier to visually identify the midpoint time of the sleep period. For example, such information may be useful for medical treatment and counseling on a basis of the midpoint time of the sleep period.

Second Embodiment

According to a second embodiment, a description is given of an example in which multiple time series graphs illustrated in the first embodiment are displayed vertically in parallel.

Figure 10A:
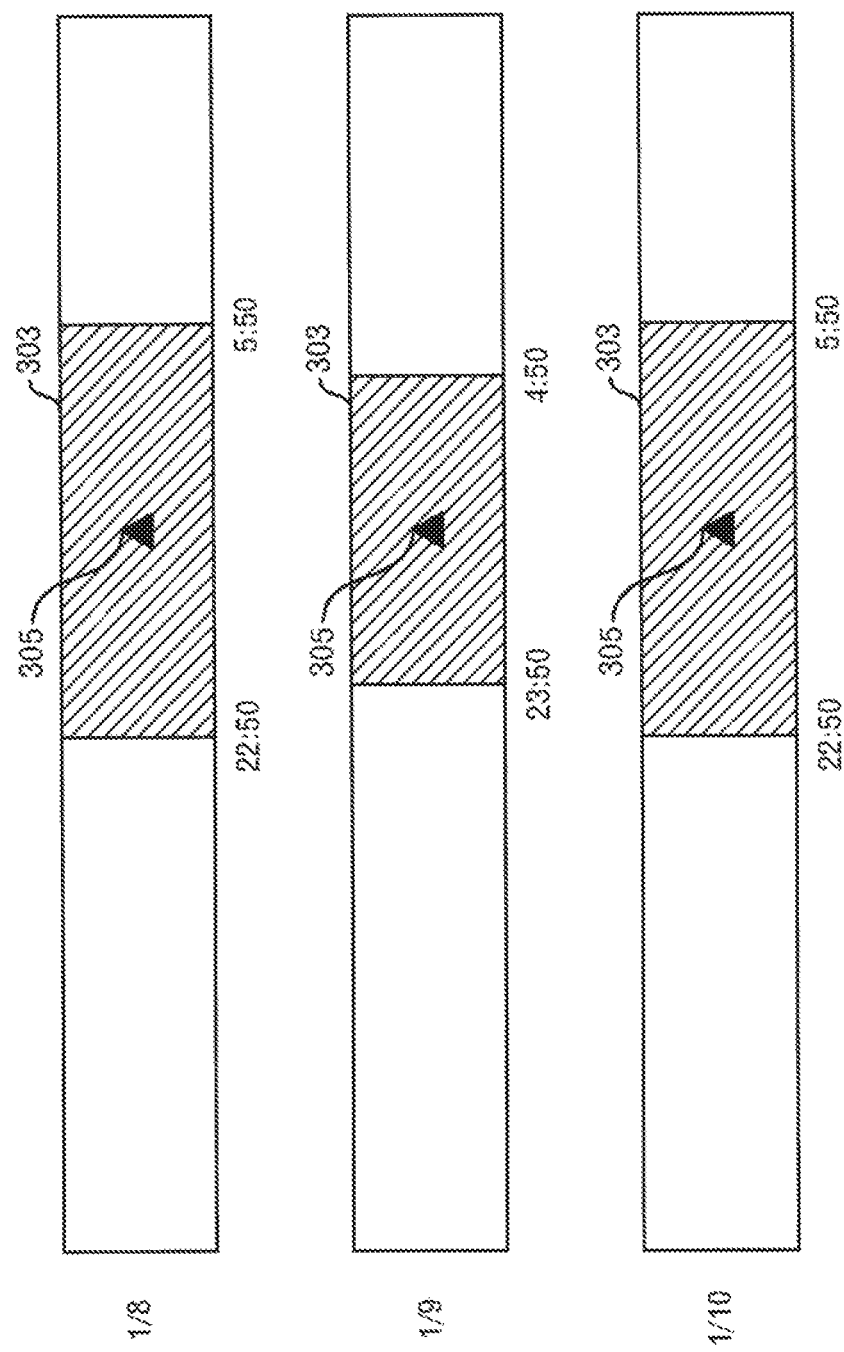
FIG. 10A is a diagram illustrating an examples of a set of time series graphs according to a second embodiment.

FIGS. 10A and 10B illustrate examples of time series graphs in the second embodiment. The bar charts 301 and a time scale are omitted from the time series graphs of these examples. In the second embodiment, time series graphs corresponding to multiple dates are displayed vertically in parallel. In the both examples illustrated in FIGS. 10A and 10B, the sleep period on January $8^{th}$ was seven hours, the sleep period on January $9^{th}$ was five hours, and the sleep period on January $10^{th}$ was seven hours.

In the example illustrated in FIG. 10A, although the sleep period is not constant for three days (on January 8, January 9, and January 10), a midpoint time of the sleep period is constant for the three days. In this example, an awake period on January $8^{th}$ is 18 hours from 5:50 to 23:50.

Likewise, the awake period on January $9^{th}$ is 18 hours from 4:50 to 22:50. That is, the length of the wake period is constant.

By contrast, in the example illustrated in FIG. 10B, the sleep period is not constant for three days (on January 8, January 9, and January 10), and a midpoint time of a sleep period is not constant. In this example, the awake period on January $8^{th}$ is 19 hours from 5:50 to 0:50 the following day. The awake period on January $9^{th}$ is 17 hours from 5:50 to 22:50. That is, the length of the awake period is not constant.

In one aspect, a stable midpoint time of the sleep period indicates that the length of the awake period is stable, and that fatigue is unlikely to accumulate. By contrast, an unstable midpoint time of the sleep period indicates that the length of the awake period varies and that fatigue is likely to accumulate. In addition, in terms of internal body cycles, the more stable the midpoint time of the sleep period, the healthier the status.

Figure 11:
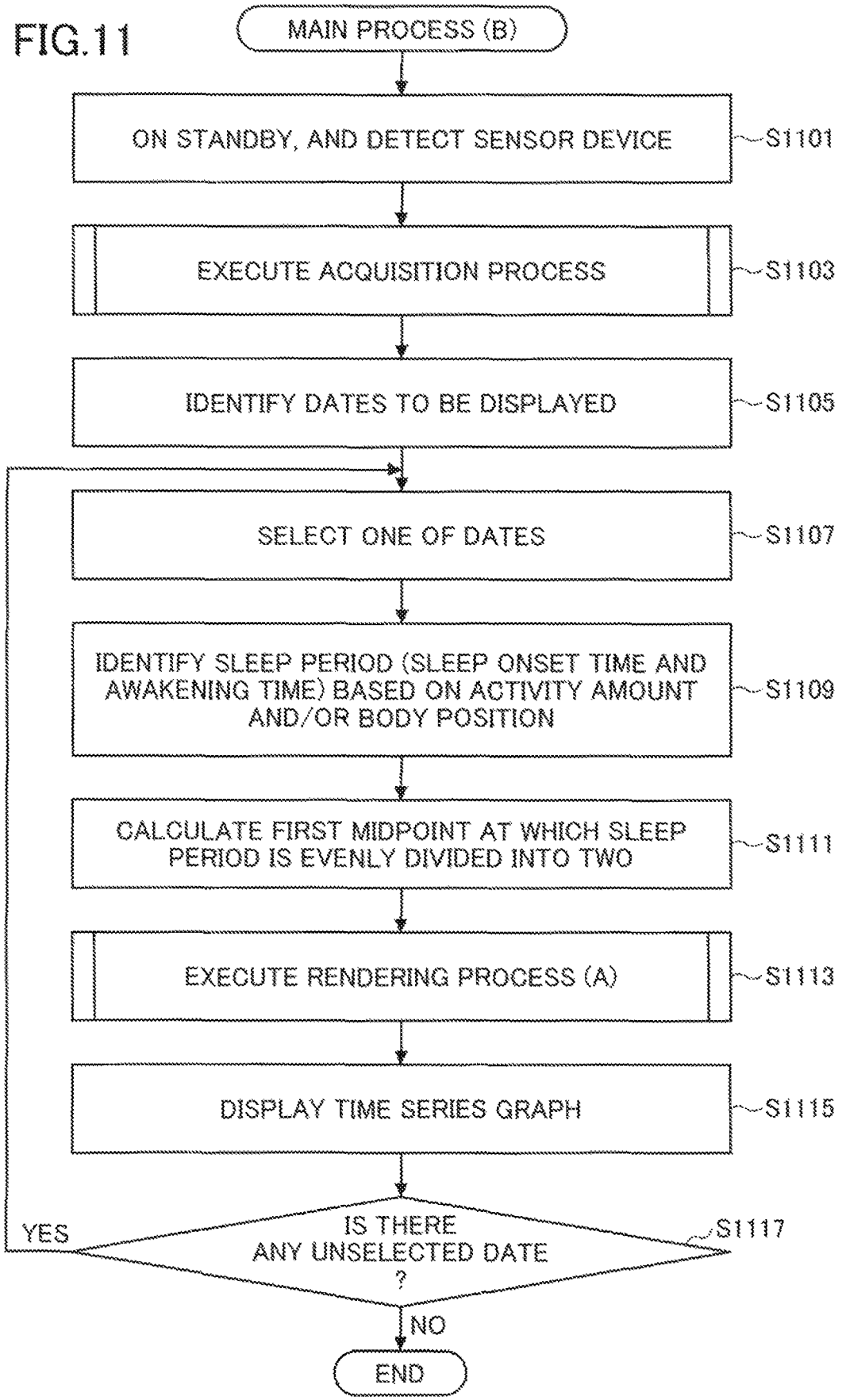
FIG. 11 is a diagram illustrating a flowchart of a main process (B)

In this second embodiment, a main process (B) is performed. FIG. 11 illustrates a flowchart of the main process (B). Steps in S1101 and S1103 are the same as steps in S601 and S603 of FIG. 6. Note that the time series data corresponding to the dates before a current date is assumed to have already been obtained. If data that has not yet been acquired from among the preceding time series data remains, the acquisition unit 403 may acquire the data in S1103.

The second identifier 415 identifies dates to be displayed (S1105). For example, the second identifier 415 identifies dates of a predetermined number of days tracing back from a current day to the current day. Note that the identified dates may be non-consecutive. For example, the identified dates may be restricted to holidays, working days, or dates relating to a particular working arrangement.

A second table used when dates are restricted to holidays, working days, or dates relating to a particular working arrangement will be described. FIG. 12 illustrates an example of the second table. The second table in this example has records corresponding to dates. Each record of the second table includes a field in which a date is set, a field in which a period covered is set, a field in which a holiday/working day distinction is set, and a field in which a working arrangement is set.

The period covered is a period managed according to these dates. The holiday/working day distinction indicates whether each of the dates corresponds to a user's holiday or working day. The working arrangement identifies a timeframe of working hours of the corresponding date. When the working hours are constant, the working arrangement may not be set.

Figure 13:
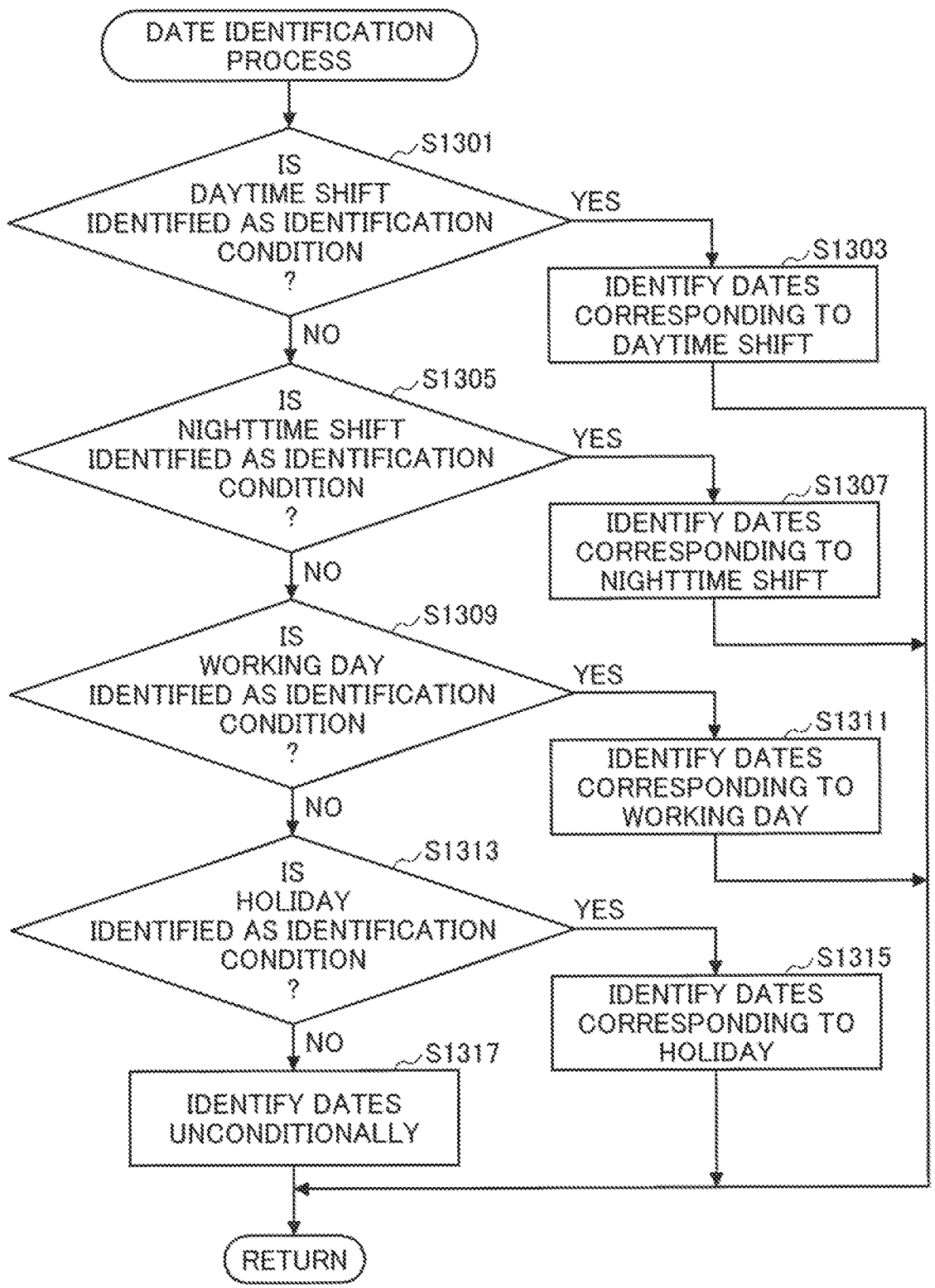
FIG. 13 is a diagram illustrating a flowchart of a date identification process.

The following illustrates, with reference to FIG. 13, a date identification process that identifies a date pertaining to a holiday, working day, and specific working arrangement. To restrict a target date, identification conditions may be designated in advance. Alternatively, identification conditions may be switched by a user's instructions.

The second identifier 415 determines whether a daytime shift is identified as an identification condition (S1301). When the second identifier 415 determines that the daytime shift is identified as an identification condition, the second identifier 415 may identify dates corresponding to the daytime shift (S1303). Specifically, the second identifier 415 may identify dates corresponding to the daytime shift for a predetermined number of days by tracing each day back from a reference date (e.g., the date of the current day).

By contrast, when the second identifier 415 determines that the daytime shift is not identified as an identification condition, the second identifier 415 determines whether a nighttime shift is identified as an identification condition (S1305). When the second identifier 415 determines that the nighttime shift is identified as an identification condition, the second identifier 415 may identify dates corresponding to the nighttime shift (S1307). Specifically, the second identifier 415 may identify dates corresponding to the nighttime shift for a predetermined number of days by tracing each day back from a reference date.

By contrast, when the second identifier 415 determines that the nighttime shift is not identified as an identification condition, the second identifier 415 determines whether a working day is identified as an identification condition (S1309). When the second identifier 415 determines that a working day is identified as an identification condition, the second identifier 415 may identify dates corresponding to a working day (S1311). Specifically, the second identifier 415 may identify dates corresponding to a working day for a predetermined number of days by tracing each day back from a reference date.

By contrast, when the second identifier 415 determines that a working day is not identified as an identification condition, the second identifier 415 determines whether a holiday is identified as an identification condition (S1313). When the second identifier 415 determines that a holiday is identified as an identification condition, the second identifier 415 may identify dates corresponding to a holiday (S1315). Specifically, the second identifier 415 may identify dates corresponding to a holiday for a predetermined number of days by tracing each day back from a reference date.

By contrast, when the second identifier 415 determines that a holiday is not identified as an identification condition, the second identifier 415 unconditionally identifies dates (S1317). Specifically, the second identifier 415 may identify a predetermined number of consecutive dates by tracing each day back from a reference date.

To identify multiple dates in the embodiments described below, the date identification process illustrated in FIG. 13 may be performed.

The following description is given by referring back to FIG. 11. The repetition controller 417 selects one of dates identified in S1105 (S1107). For example, dates are identified in chronological order.

The first identifier 405 identifies a sleep period (a sleep onset time and an awakening time), based on time series data of the activity amount and/or body positions on the corresponding date (S1109).

The first calculator 407 calculates the first midpoint at which the sleep period is evenly divided into two as in the case of S607 illustrated in FIG. 6 (S1111).

The rendering unit 411 executes the rendering process (A) as in the case of S609 illustrated in FIG. 6 (S1113). When another time series graph has already been displayed, the display processor 413 displays a time series graph of the corresponding date such that the time axis of the time series graph of the corresponding date is displayed parallel to the time axis of the already displayed time series graph, and times of the respective time series graphs are aligned vertically with respect to the time axis (S1115).

The repetition controller 417 determines whether there is an unselected date (S1117). When the repetition controller 417 determines that there is an unselected date, the repetition controller 417 returns to step S1107 and repeats the process from step S1107. By contrast, when the repetition controller 417 determines that there is no unselected date, the repetition controller 417 ends the main process (B).

According to the second embodiment, it is easier to visually identify stability of the midpoint time of a sleep period.

In addition, the date identification process is enabled to exclude sleep periods corresponding to different working conditions from among the sleep periods subject to processing.

Third Embodiment

Although the above-described embodiments illustrate an example of displaying the midpoint time of the sleep period, a third embodiment illustrates an example of further displaying the midpoint time of a stay-in-bed period.

Figure 14:
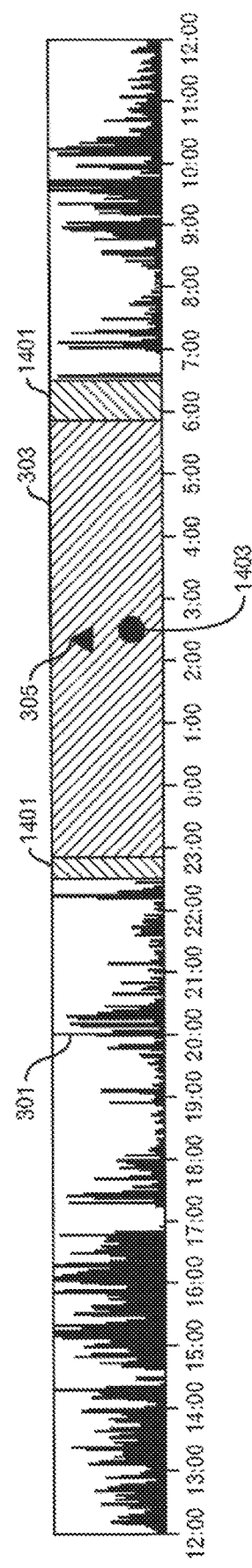
FIG. 14 is a diagram illustrating an example of a time series graph according to a third embodiment.

FIG. 14 illustrates an example of a time series graph according to the third embodiment. As in FIG. 3, the amount of activity from a predetermined start time to a predetermined end time is represented by a bar chart 301. The first band chart 303 of the sleep period and the first mark 305 indicating the midpoint time of the sleep period are the same as in FIG. 3. In the example of FIG. 14, the stay-in-bed period corresponding to the awake status is indicated by a second band chart 1401. The second band chart 1401 indicates a period from a time of getting into bed to a time of falling asleep, and also indicates a period from an awakening time to a time of getting out of bed. In addition, a second mark 1403 indicating the midpoint time of the stay-in-bed period is also displayed.

As illustrated in the example of FIG. 14, the second mark 1403 being located after the first mark 305 indicates that a user awakens earlier. By contrast, the second mark 1403 being located before the first mark 305 indicates that a user has poor sleep. That is, a positional relationship between the first mark 305 and the second mark 1403 facilitates identification of a tendency toward insomnia and degree of insomnia at first glance.

FIG. 15 illustrates an example of a first table according to the third embodiment. Events in the third embodiment are any one of getting into bed, falling asleep (sleep onset), awakening, and getting out of bed.

Figure 16:
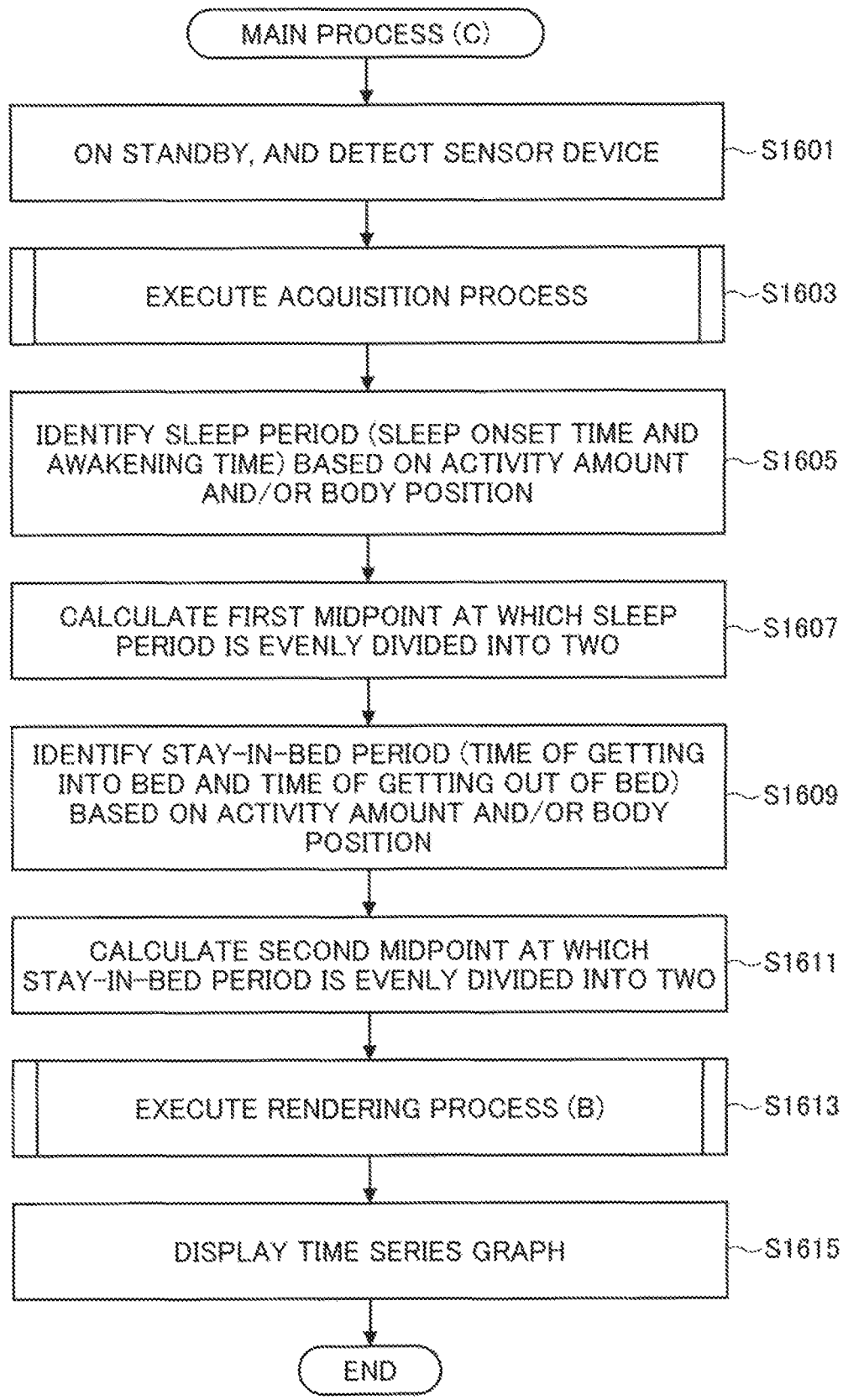
FIG. 16 is a diagram illustrating a flowchart of a main process (C)

In this third embodiment, a main process (C) is performed. FIG. 16 illustrates a flowchart of the main process (C). Steps in S1601 to S1607 are the same as steps in S601 to S607 of FIG. 6.

The third identifier 419 identifies a stay-in-bed period (a time of getting into bed and a time of getting out of bed), based on time series data of the activity amount and/or time series data of body positions (S1609).

The second calculator 421 calculates a second midpoint at which the stay-in-bed period is evenly divided into two (S1611). Specifically, a time (time point) at the second midpoint is obtained by adding a time (time interval) equivalent to half the length of the stay-in-bed period to a time (time point) of getting into bed. Alternatively, a time at the second midpoint may be obtained by subtracting a time (time interval) equivalent to half the length of the stay-in-bed period from a time (time point) of getting out of bed.

The rendering unit 411 executes a rendering process (B) (S1613). In the rendering process (B), a time series graph illustrated in FIG. 14 is rendered.

Figure 17:
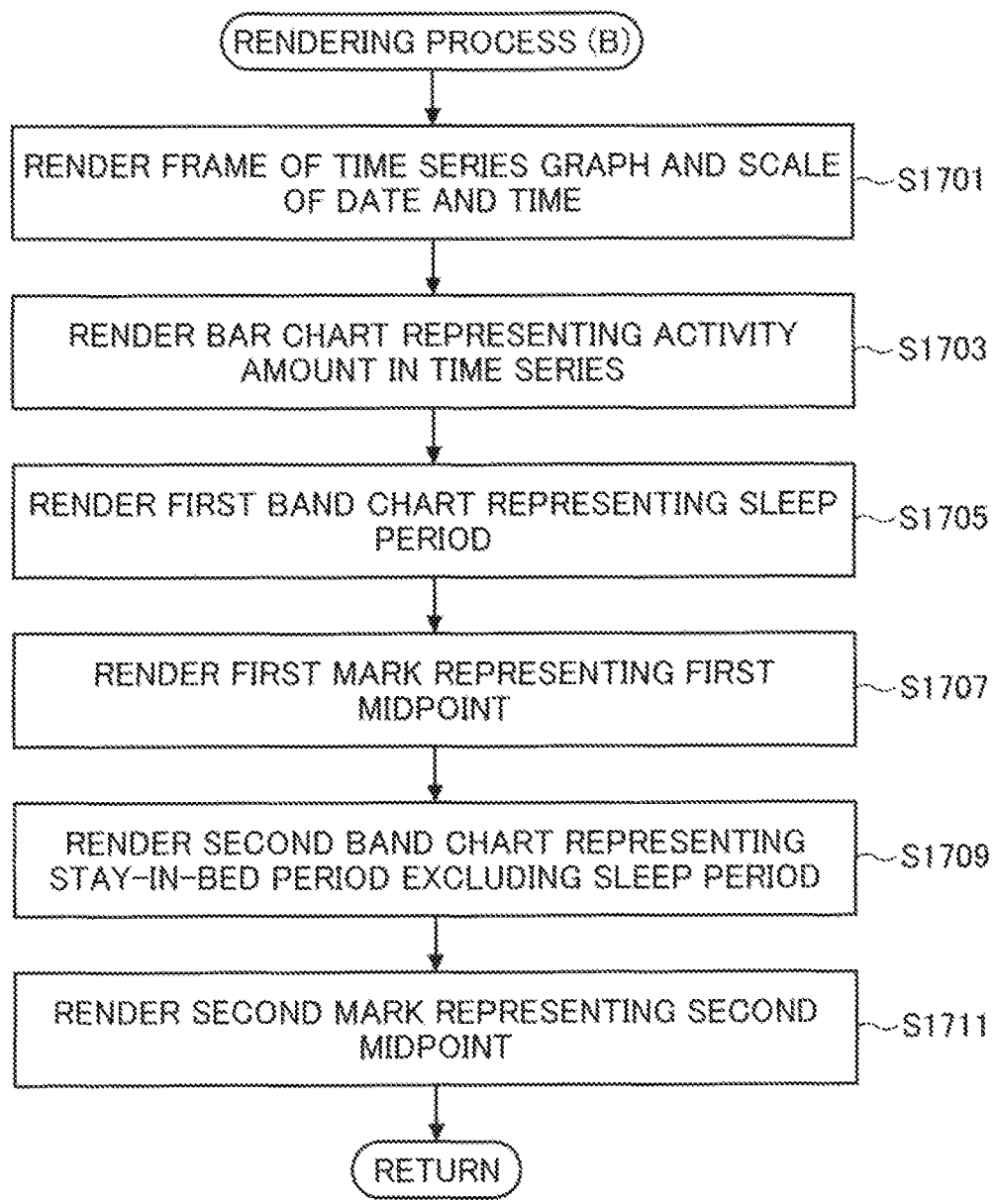
FIG. 17 is a diagram illustrating a flowchart of a rendering process (B)

FIG. 17 illustrates a flowchart of the rendering process (B). Steps in S1701 to S1707 are the same as steps in S801 to S807 of FIG. 8.

The rendering unit 411 renders a second band chart representing the stay-in-bed period excluding the sleep period (S1709). Specifically, the rendering unit 411 renders the second band chart 1401 indicating an interval between the time of getting into bed and the time of falling asleep (sleep onset time), and the second band chart 1401 indicating an interval between the awakening time and the time of getting out of bed. The rendering unit 411 renders a second mark 1403 representing the second midpoint at a position corresponding to the second midpoint (S1711). The rendered images of a frame, date and time, bar chart 301, first band chart 303, first mark 305, second bar chart 1401, and second mark 1403 are stored in the image buffer 437. When the rendering process (B) ends, the process returns to the invoking source main process (C).

The following description is given by referring back to FIG. 16. In S1615, the display processor 413 displays a time series graph. Specifically, the display processor 413 displays the images of the frame, date and time, bar chart 301, first band chart 303, first mark 305, second band chart 1401, and second mark 1403 rendered in the rendering process (B) on the display device 455. Then, the main process (C) ends.

Figure 18:
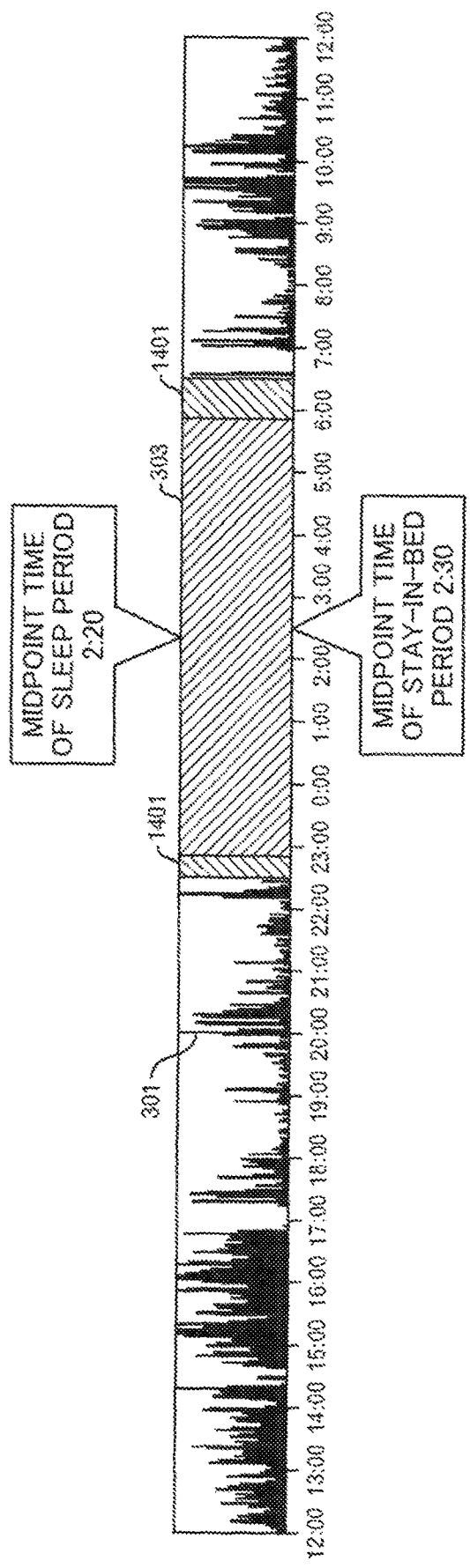
FIG. 18 is a diagram illustrating an example of a time series graph according to the third embodiment.

In the example described above, a second mark 1403 is rendered at a position corresponding to the second midpoint. However, other display elements such as lines may be rendered and displayed. Further, as illustrated in FIG. 18, the output processor 409 may display a time at the second midpoint in a balloon, for example, with numerals or other symbols (or numerals and characters).

According to the third embodiment, it is easier to visually identify the midpoint time of the stay-in-bed period. For example, such information processing apparatus may be useful for medical treatment and counseling on a basis of the midpoint time of the stay-in-bed period.

It is also easier to identify an interrelationship between the midpoint time of the sleep period and the midpoint time of the stay-in-bed period. For example, such information may be useful for medical treatment and counseling on a basis of an interrelationship between the midpoint time of the sleep period and the midpoint time of the stay-in-bed period.

Fourth Embodiment

According to a fourth embodiment, a description is given of an example in which multiple time series graphs illustrated in the third embodiment are displayed vertically in parallel.

Figure 19:
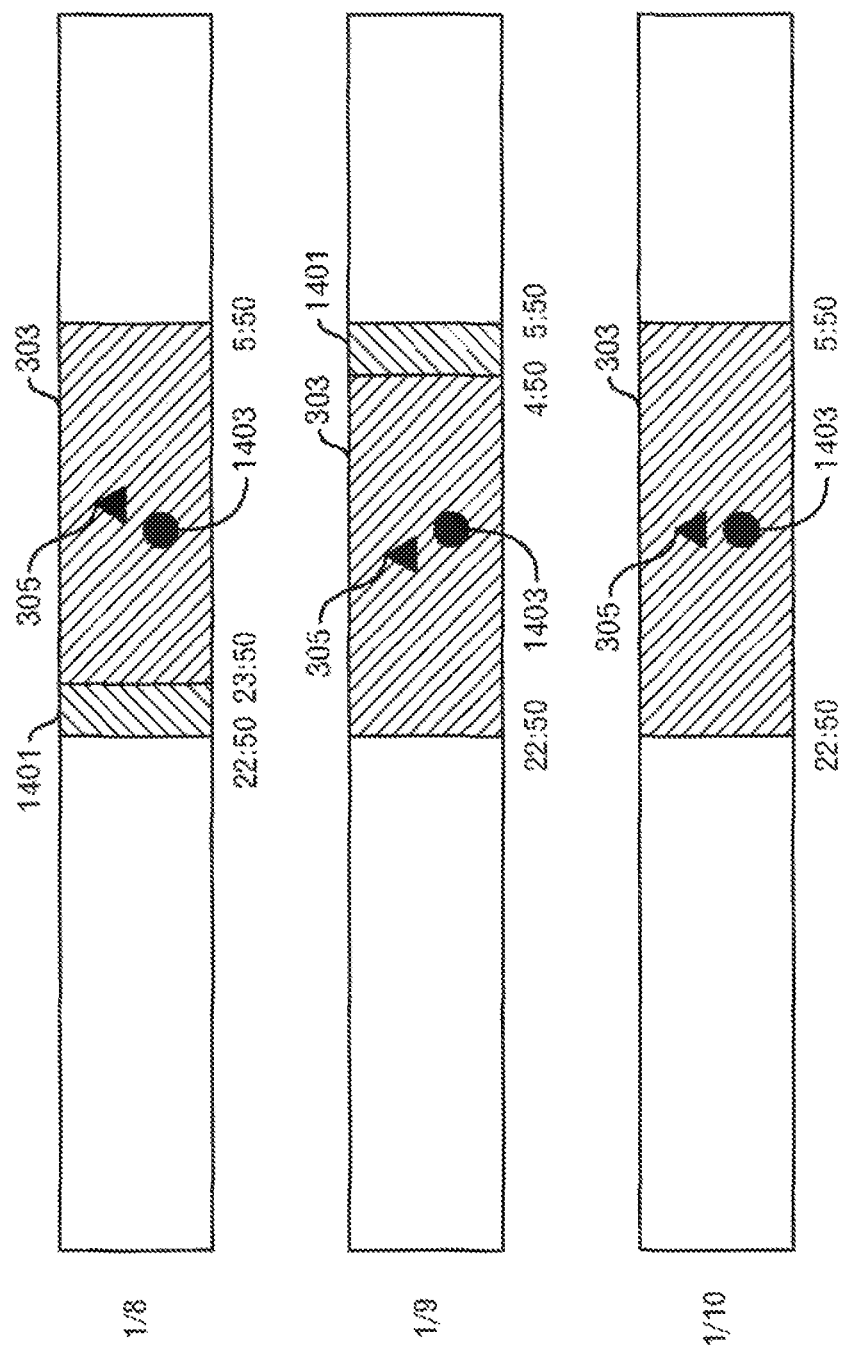
FIG. 19 is a diagram illustrating an example of a time series graph according to a fourth embodiment.

FIG. 19 illustrates an example of a set of time series graphs according to the third embodiment. The bar charts 301 and a time scale are omitted. According to this example, on January $8^{th}$, a user had poor sleep. On January $9^{th}$, the user was not asleep in the early morning. On January $10^{th}$, the user had good sleep and was asleep in the early morning. In this example, a sleep status is not stable for three days (January $8^{th}$, January $9^{th}$, and January $10^{th}$).

However, the time of getting into bed and the time of getting out of bed are stable. When a stay-in-bed period (the time of getting into bed and the time of getting out of bed are regular) is regular as in the example above, positions of the second mark 1403 on the above dates are vertically aligned. Displaying the second marks 1403 vertically in parallel in this manner makes it easier to identify the regularity of the stay-in-bed period at first glance. If the length of stay-in-bed period is regular, the activity period is also regular.

By contrast, if the length of stay-in-bed period is irregular, the activity period is also irregular, and an internal body cycle is likely to be unstable. When positions of the second mark 1403 are unaligned, there may be lifestyle-relating issues such as, for example, staying up late at night.

Figure 20A:
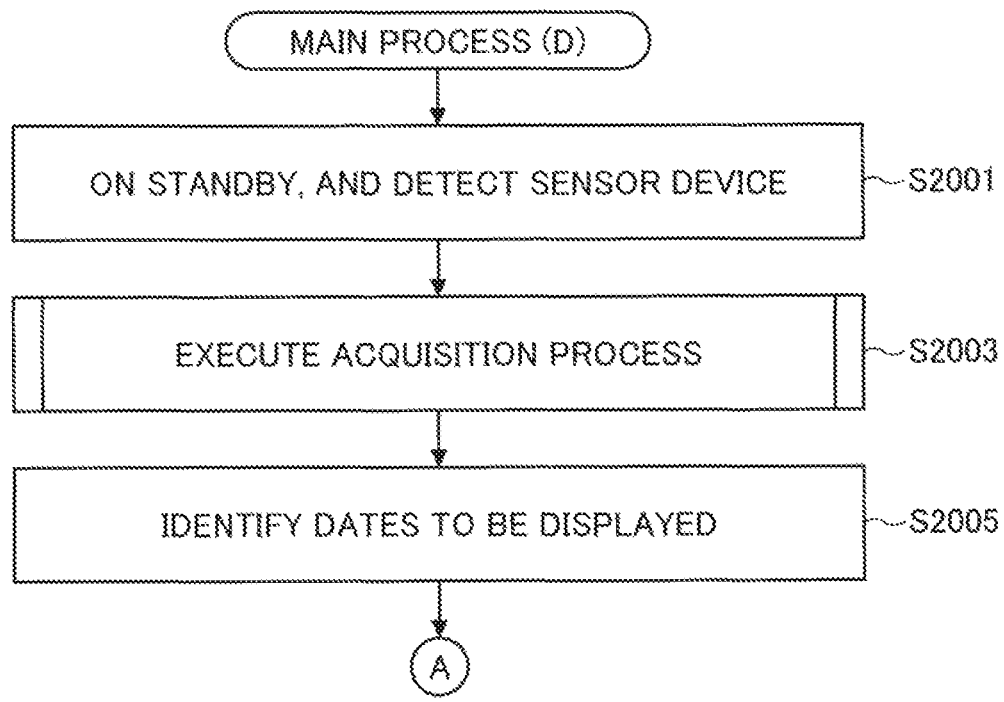
FIG. 20A is a diagram illustrating a flowchart of a main process (D)
Figure 20B:
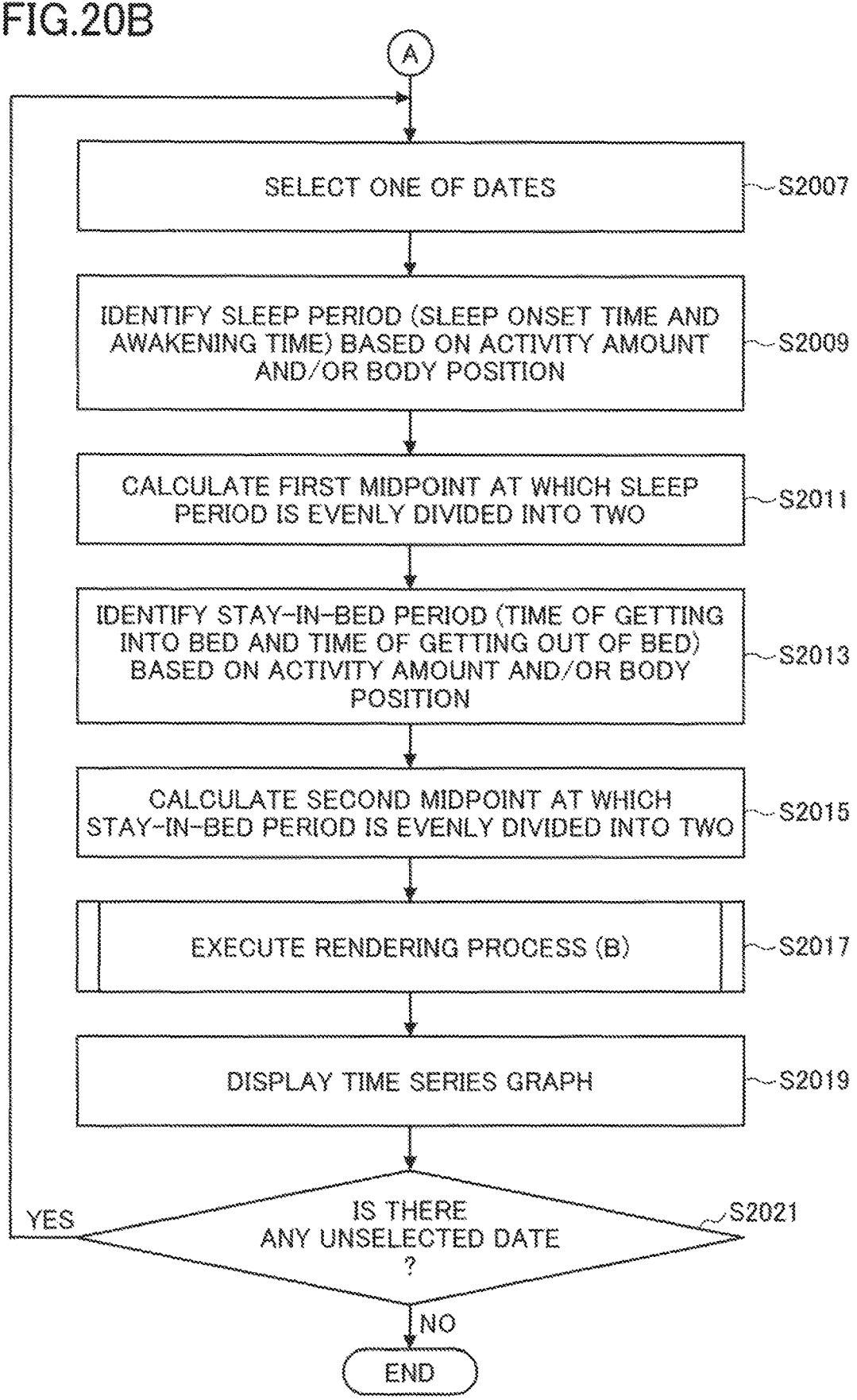
FIG. 20B is a diagram illustrating another flowchart of the main process (D)

In this fourth embodiment, a main process (D) is performed. FIGS. 20A and 20B illustrate a flowchart of the main process (D). Steps in S2001 and S2003 are the same as steps in S601 and S603 of FIG. 6. Further, step S2005 is the same as step S1105 of FIG. 11.

After step S2005 ends, step S2007 of FIG. 20B is processed through a terminal A. Steps in S2007 to S2011 are the same as steps in S1107 to S1111 of FIG. 11.

The third identifier 419 identifies a stay-in-bed period (a time of getting into bed and a time of getting out of bed), based on time series data of the activity amount and/or time series data of body positions on the date selected in step S2007 (S2013).

The second calculator 421 calculates a second midpoint at which the stay-in-bed period is evenly divided by two, in the same manner as in the case S1611 illustrated in FIG. 16 (S2015).

The rendering unit 411 executes the rendering process (B) as in the case of S1613 illustrated in FIG. 16 (S2017).

When another time series graph has already been displayed, the display processor 413 displays a time series graph of the corresponding date such that the time axis of the time series graph of the corresponding date is displayed parallel to the time axis of the already displayed time series graph, and times of the respective time series graphs are aligned vertically with respect to the time axis (S2019).

The repetition controller 417 determines whether there is an unselected date (S2021). When the repetition controller 417 determines that there is an unselected date, the repetition controller 417 returns to step S2007 and repeats the process from step S2007. By contrast, when the repetition controller 417 determines that there is no unselected date, the repetition controller 417 ends the main process (D).

According to the fourth embodiment, it is easier to visually identify stability of the midpoint time of the stay-in-bed period.

Fifth Embodiment

The following fifth to twelfth embodiments illustrate examples of evaluating the quality of sleep. In the fifth embodiment, an example of evaluating the quality of sleep based on the difference in the midpoint time between two sleep periods will be described.

Figure 21:
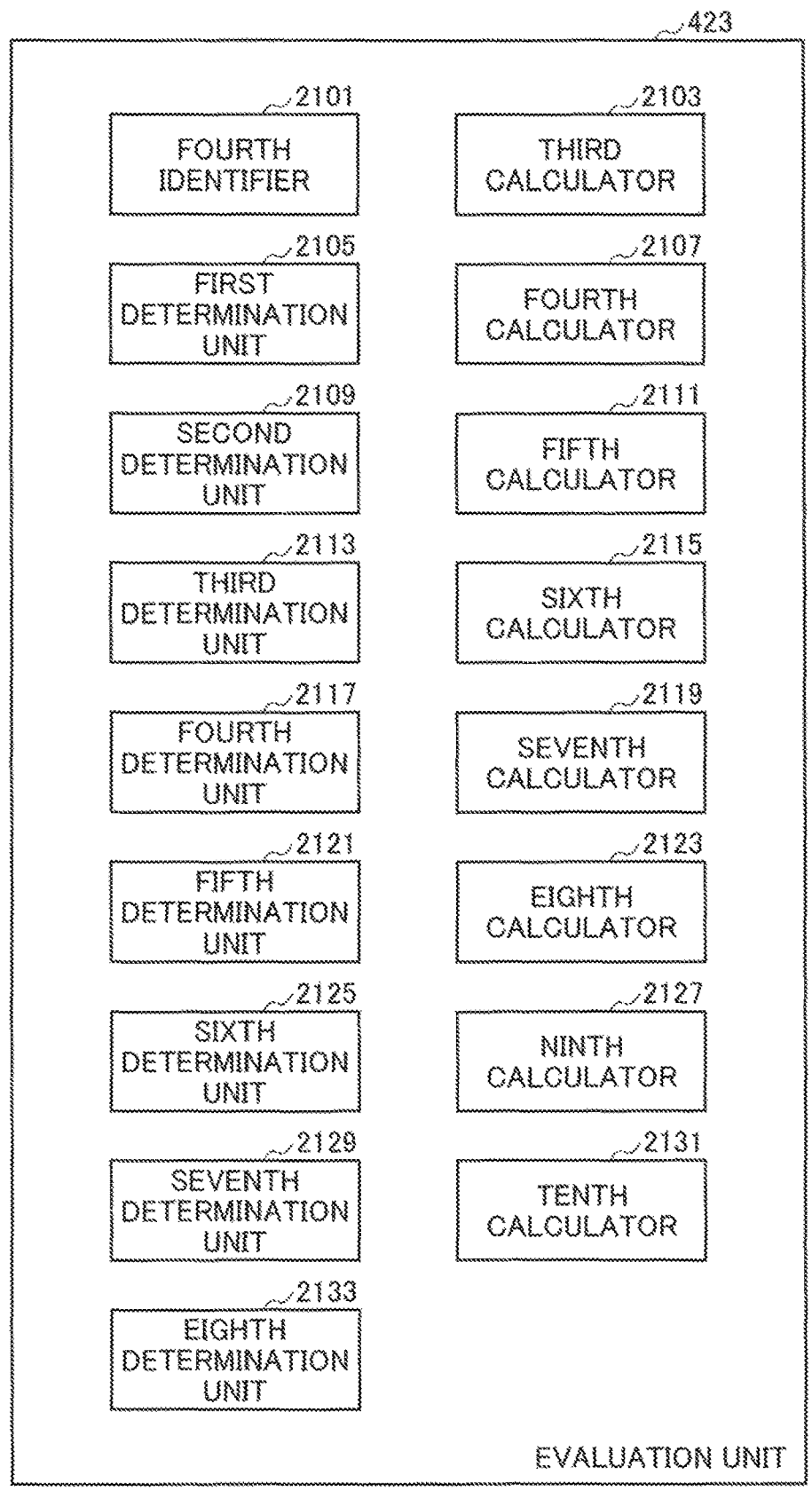
FIG. 21 is a diagram illustrating an example of a module configuration of an evaluation unit.

FIG. 21 illustrates an example of a module configuration of an evaluation unit 423 according to the fifth to twelfth embodiments. The evaluation unit 423 includes a fourth identifier 2101, a third calculator 2103, a first determination unit 2105, a fourth calculator 2107, a second determination unit 2109, a fifth calculator 2111, a third determination unit 2113, a sixth calculator 2115, a fourth determination unit 2117, a seventh calculator 2119, a fifth determination unit 2121, an eighth calculator 2123, a sixth determination unit 2125, a ninth calculator 2127, a seventh determination unit 2129, a tenth calculator 2131, and an eighth determination unit 2133.

In the fifth to tenth and twelfth embodiments, the fourth identifier 2101 identifies dates to be compared or dates to be analyzed.

In the fifth embodiment, the third calculator 2103 calculates a first time difference. The first time difference will be described later. The first determination unit 2105 makes a determination on evaluation of the quality of sleep based on the first time difference.

In the sixth embodiment, the fourth calculator 2107 calculates a second time difference. The second time difference will be described later. The second determination unit 2109 makes a determination on evaluation of the quality of sleep based on the second time difference.

In the seventh embodiment, the fifth calculator 2111 calculates a first index representing a variability of times at the first midpoints. The third determination unit 2113 makes a determination on evaluation of the quality of sleep based on the first index.

In the eighth embodiment, the sixth calculator 2115 calculates a second index representing a variability of times at the second midpoints. The fourth determination unit 2117 makes a determination on evaluation of the quality of sleep based on the second index.

In the ninth embodiment, the seventh calculator 2119 calculates a third index representing a variability of the first time differences. The fifth determination unit 2121 makes a determination on evaluation of the quality of sleep based on the third index.

In the tenth embodiment, the eighth calculator 2123 calculates a fourth index representing a variability of the second time differences. The sixth determination unit 2125 makes a determination on evaluation of the quality of sleep based on the fourth index.

In the eleventh embodiment, the ninth calculator 2127 calculates a third time difference. The third time difference will be described later. The seventh determination unit 2129 makes a determination on evaluation of the quality of sleep based on the third time difference.

In the twelfth embodiment, the tenth calculator 2131 calculates a fifth index representing a variability of the third time differences. The eighth determination unit 2133 makes a determination on evaluation of the quality of sleep based on the fifth index.

The fourth identifier 2101, the third calculator 2103, the first determination unit 2105, the fourth calculator 2107, the second determination unit 2109, the fifth calculator 2111, the third determination unit 2113, the sixth calculator 2115, the fourth determination unit 2117, the seventh calculator 2119, the fifth determination unit 2121, the eighth calculator 2123, the sixth determination unit 2125, the ninth calculator 2127, the seventh determination unit 2129, the tenth calculator 2131, and the eighth determination unit 2133 described above are implemented using a hardware resource (e.g., FIG. 35) and a program that causes processors to execute a process described below.

Figure 22:
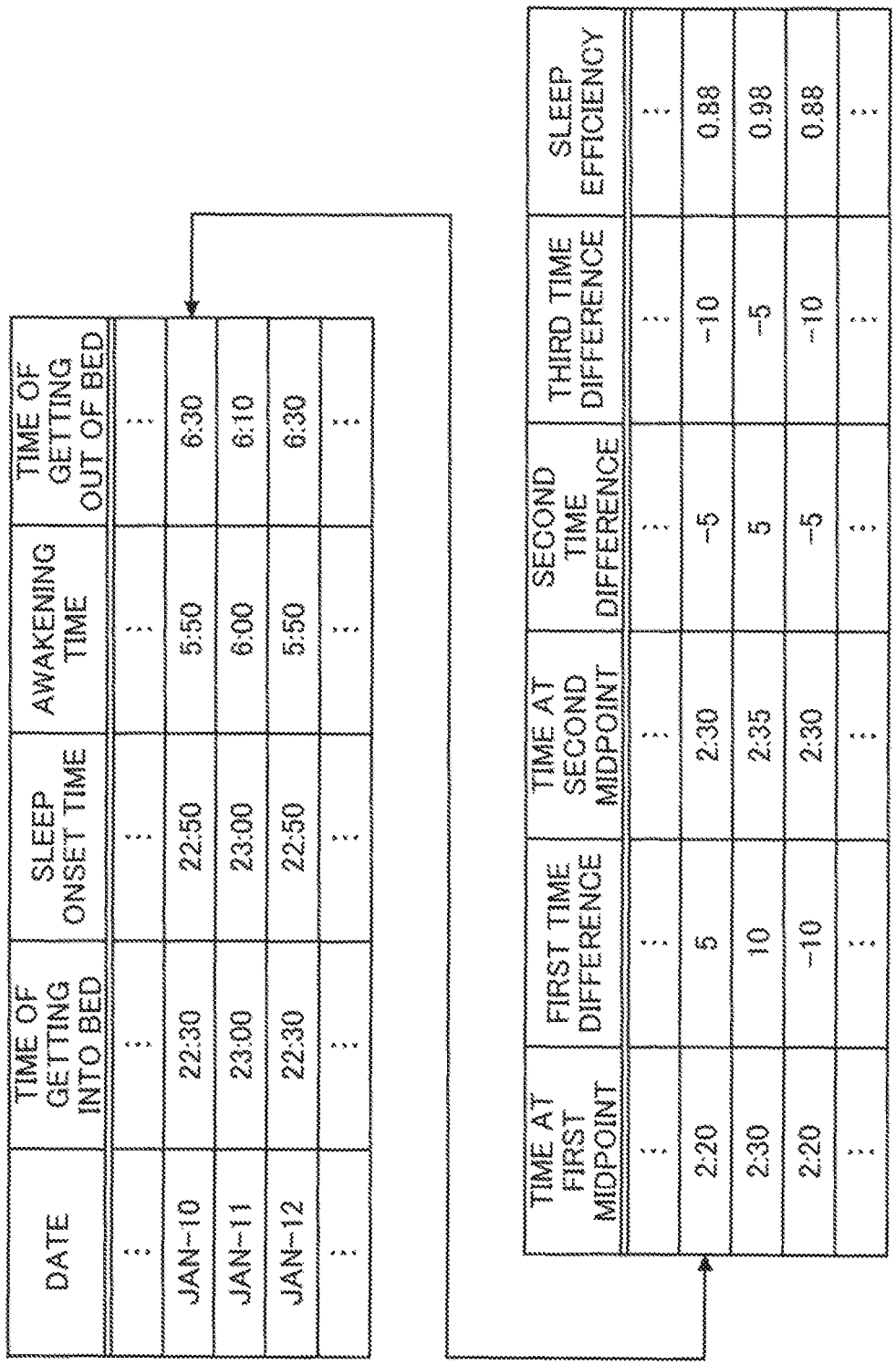
FIG. 22 is a diagram illustrating an example of a third table.

The following describes, with reference to FIG. 22, an example of a third table in which parameters in the fifth to twelfth embodiments are stored. The third table in this example has records each corresponding to a date and time. Each record of the third table includes a field in which a date is stored, a field in which a time of getting into bed is stored, a field in which a time of falling asleep (sleep onset time) is stored, a field in which an awakening time is stored, a field in which a time of getting out of bed is stored, a field in which a time at a first midpoint is stored, a field in which a first time difference is stored, a field in which a time at a second midpoint is stored, a field in which a second time difference is stored, a field in which a third time difference is stored, and a field in which sleep efficiency is stored.

The sleep onset time and the awakening time are already calculated in any of the main processes (A) to (D) and stored in the corresponding fields in the main process.

The time of getting into bed and the time of getting out of bed are already calculated in either of the main process (C) or (D) and stored in the corresponding fields in the main process. If the time of getting into bed and the time of getting out of bed are not set, the time of getting into bed and the time of getting out of bed may be identified in the evaluation process and may be stored in the corresponding fields.

The time at the first midpoint is already calculated in any of the main processes (A) to (D) and stored in the field of the time at the first midpoint in the main process.

The first time difference is a time difference obtained by subtracting a time at the first midpoint on the second date from a time at the first midpoint on the first date. The second date corresponds, for example, to the day before the first date.

The time at the second midpoint is already calculated in either of the main process (C) or (D) and stored in the field of the time at the second midpoint in the main process. If the second midpoint is not set, the second midpoint may be calculated in the evaluation process and may be stored in the corresponding field.

The second time difference is a time difference obtained by subtracting a time at the second midpoint on the second date from a time at the second midpoint on the first date.

The third time difference is a difference in time obtained by subtracting a time at the first midpoint from a time at the second midpoint for one stay-in-bed period. When sleeping poorly, the third time difference is negative. When a user awakens early in the morning, the third time difference is a positive value.

Sleep efficiency is a value obtained by dividing a length of a sleep period by a length of a stay-in-bed period. That is, the obtained value is equivalent to a ratio of a sleep period to a stay-in-bed period.

The third table in this example includes parameters used in the following evaluation processes (A) to (H) described in the fifth to twelfth embodiments. However, in each embodiment, the fields of the parameters not used in the evaluation process may be omitted. Parameters may also be held in a format other than a table.

The following illustrates a description of an evaluation process. In this example, an evaluation process is activated upon a user assigning an evaluation instruction to the information processing apparatus 201. However, the evaluation process is activated at any desired time. The main process may be followed by an automatic activation of the evaluation process. The same applies to an evaluation process in other embodiments. In addition, multiple evaluation processes may be interlinked.

Figure 23:
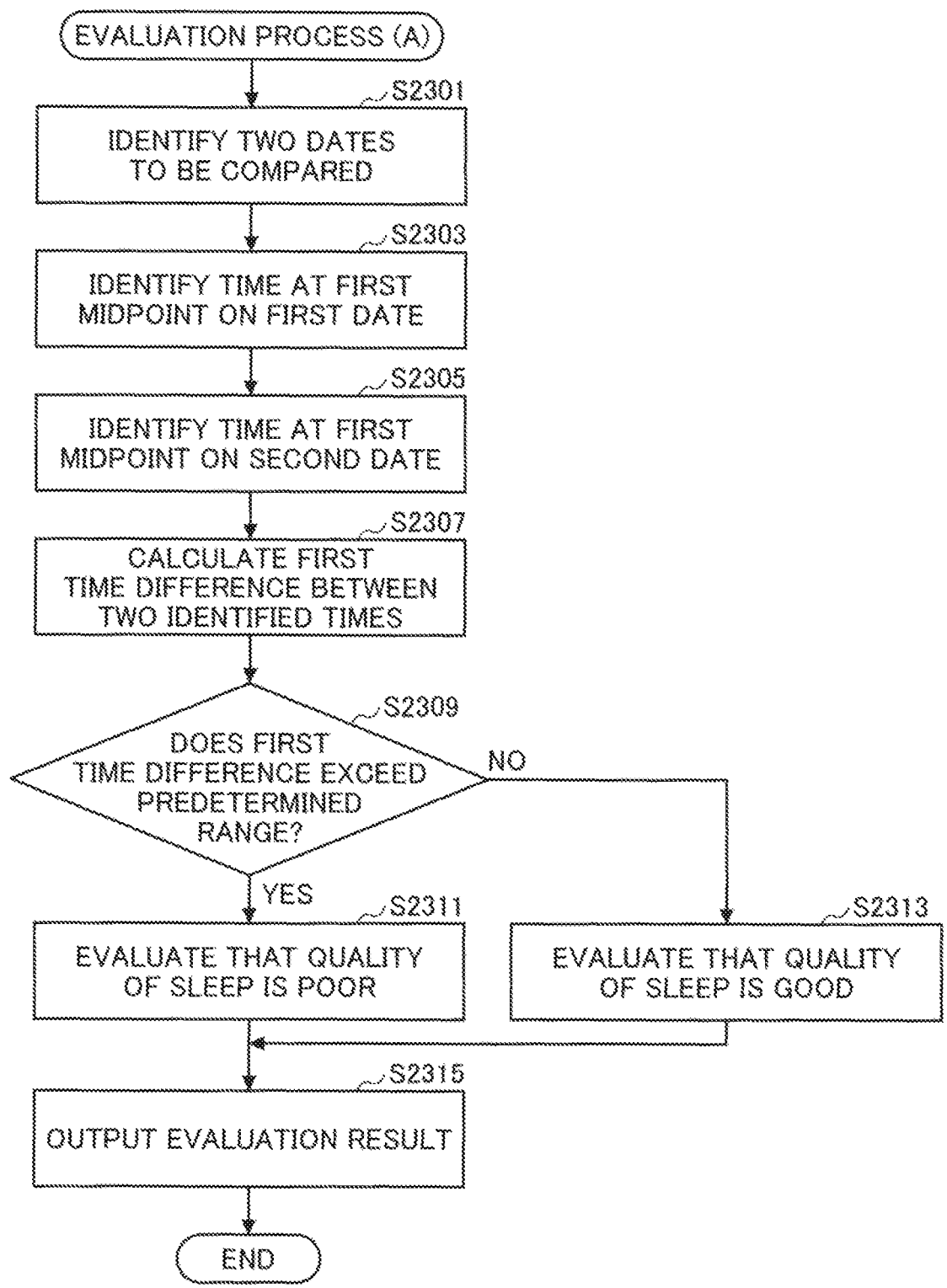
FIG. 23 is a diagram illustrating a flowchart of an evaluation process (A)

In this embodiment, an evaluation process (A) is executed. FIG. 23 illustrates a flowchart of an evaluation process (A). The fourth identifier 2101 identifies two dates to be compared (S2301). For example, the fourth identifier 2101 identifies respective dates of a current day and a preceding day. The two dates may be either continuous or discontinuous. The fourth identifier 2101 may execute a date identification process illustrated in FIG. 13.

The third calculator 2103 identifies a time at the first midpoint on a first date (S2303).

The third calculator 2103 also identifies a time at the first midpoint on a second date (S2305).

The third calculator 2103 then calculates a first time difference between two identified times (i.e., the time at the first midpoint on the first date and the time at the first midpoint on the second date) (S2307). Specifically, the first time difference is obtained by subtracting the time at the first midpoint on the second date from the time at the first midpoint on the first date.

The first determination unit 2105 determines whether the first time difference exceeds a predetermined range (S2309). The predetermined range is identified by lower and upper limits. The predetermined range may be identified by a lower limit without an upper limit. The predetermined range may be identified by an upper limit without a lower limit.

When the first determination unit 2105 determines that the first time difference exceeds the predetermined range, the first determination unit 2105 evaluates that the quality of sleep is poor (S2311). When the first determination unit 2105 determines that the first time difference does not exceed the predetermined range, the first determination unit 2105 evaluates that the quality of sleep is good (S2313).

The output processor 409 outputs an evaluation result in S2311 or S2313 (S2315). Specifically, the output processor 409 displays the evaluation result on the display device 455 as a comment. Then, the evaluation process (A) ends. Note that the output form of the evaluation result is not limited to display. The evaluation result may be printed. The evaluation result may be written to a storage medium. Alternatively, the evaluation result may be transmitted. The same applies to an evaluation process illustrated below.

According to the fifth embodiment, it is possible to evaluate the quality of sleep focusing on stability of a midpoint time of a sleep period.

Sixth Embodiment

According to a sixth embodiment, a description is given of an example of evaluating the quality of sleep based on a difference in a midpoint time between two stay-in-bed periods.

Figure 24:
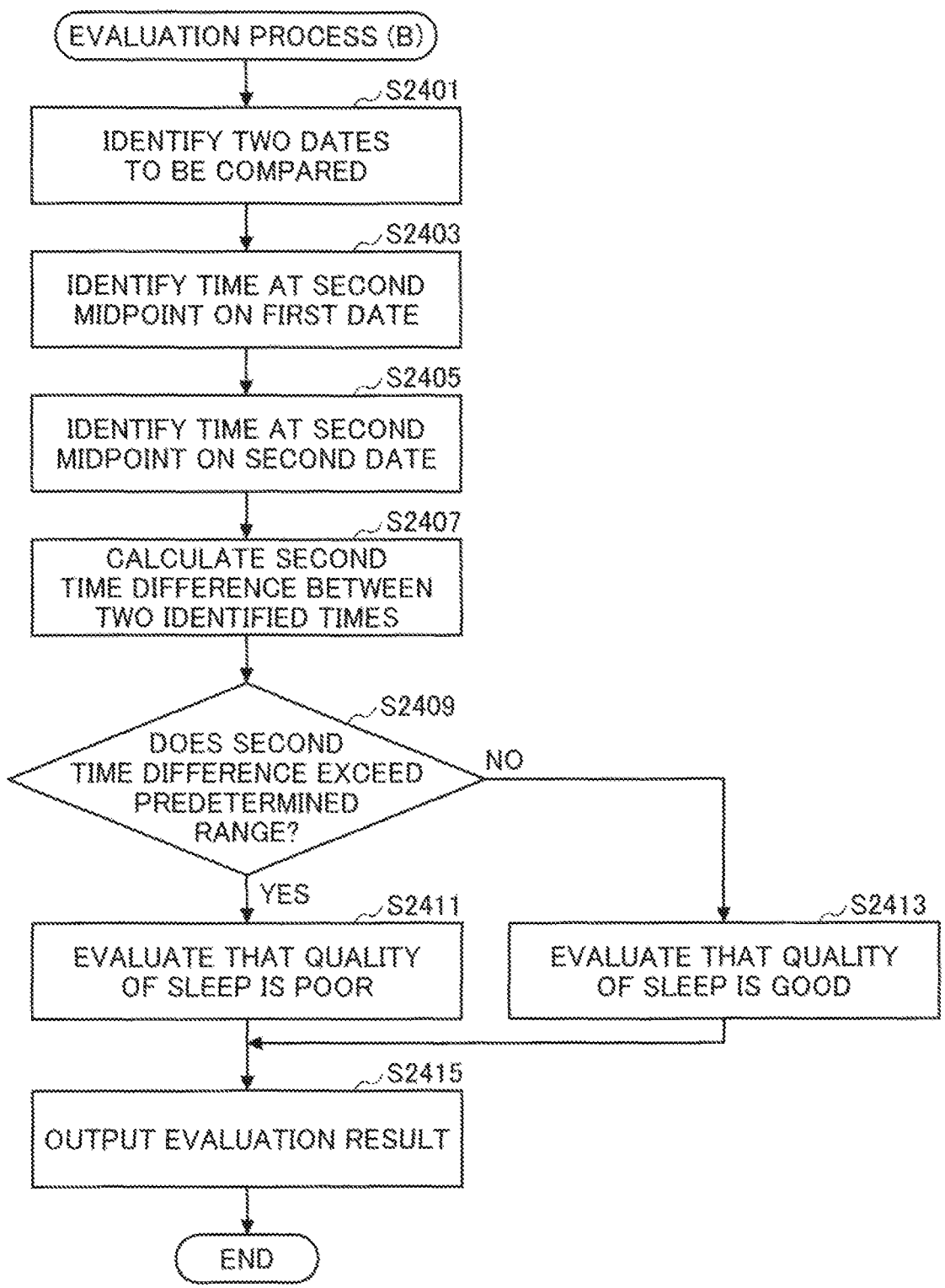
FIG. 24 is a diagram illustrating a flowchart of an evaluation process (B)

In this sixth embodiment, an evaluation process (B) is executed. FIG. 24 illustrates a flowchart of an evaluation process (B). The fourth identifier 2101, as in the case of S2301 illustrated in FIG. 23, identifies two dates to be compared (S2401).

The fourth calculator 2107 identifies a time at a second midpoint on a first date (S2403). The fourth calculator 2107 also identifies a time at a second midpoint on a second date (S2405). The fourth calculator 2107 then calculates a second time difference between the two identified times (i.e., the time at the second midpoint on the first date and the time at the second midpoint on the second date) (S2407). Specifically, the second time difference is obtained by subtracting the time at the second midpoint on the second date from the time at the second midpoint on the first date.

The second determination unit 2109 determines whether the second time difference exceeds a predetermined range (S2409). The predetermined range is identified by lower and upper limits. The predetermined range may be identified by a lower limit without an upper limit. The predetermined range may be identified by an upper limit without a lower limit.

When the second determination unit 2109 determines that the second time difference exceeds the predetermined range, the second determination unit 2109 evaluates that the quality of sleep is poor (S2411). When the second determination unit 2109 determines that the second time difference does not exceed the predetermined range, the second determination unit 2109 evaluates that the quality of sleep is good (S2413).

The output processor 409 outputs an evaluation result in S2411 or S2413 (S2415). Specifically, the output processor 409 displays the evaluation result on the display device 455 as a comment. Then, the evaluation process (B) ends.

According to the sixth embodiment, it is possible to evaluate the quality of sleep focusing on stability of a midpoint time of a stay-in-bed period.

Seventh Embodiment

According to a seventh embodiment, a description is given of an example of evaluating the quality of sleep by statistically analyzing a midpoint time of a sleep period.

Figure 25:
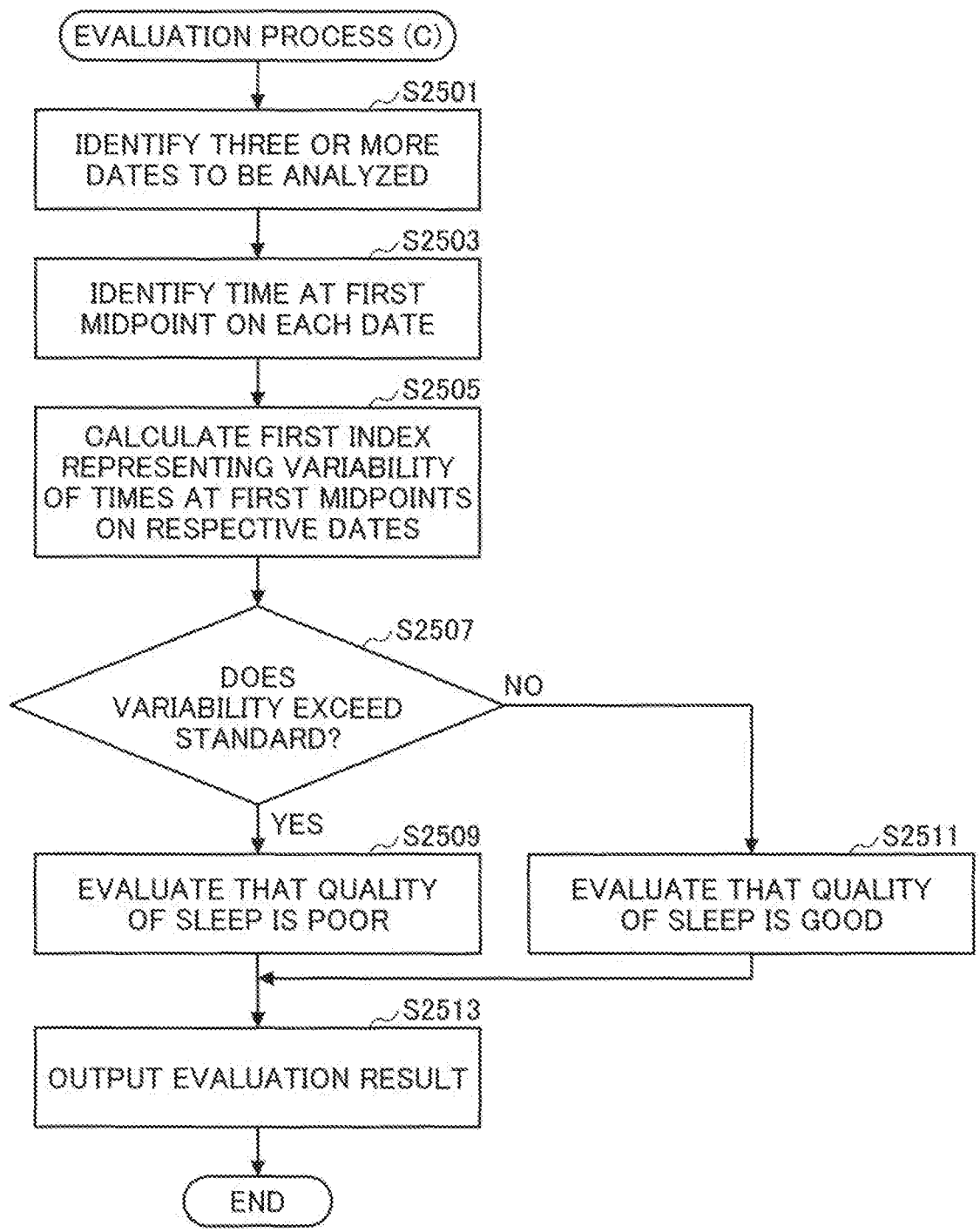
FIG. 25 is a diagram illustrating a flowchart of an evaluation process (C)

In the seventh embodiment, an evaluation process (C) is executed. FIG. 25 illustrates a flowchart of the evaluation process (C). The fourth identifier 2101 identifies three or more dates to be analyzed (S2501). For example, the fourth identifier 2101 identifies respective dates of a current day and two preceding days. The three or more dates may be either continuous or discontinuous. The fourth identifier 2101 may execute a date identification process illustrated in FIG. 13.

The fifth calculator 2111 identifies a time at the first midpoint on each date (S2503). Then, the fifth calculator 2111 calculates a first index representing a variability of the times at the respective first midpoints (S2505). The first index is, for example, the variance or standard deviation. High variance indicates a large variability. Low variance indicates a small variability. Similarly, a high standard deviation indicates a large variability. A low standard deviation indicates a small variability. Alternatively, a process capability index may be used instead of the variance or standard deviation. A low process capability index indicates a large variability. A high process capability index indicates a small variability.

The third determination unit 2113 determines whether the variability exceeds a standard (S2507). The third determination unit 2113 determines, for example, whether the variance exceeds a threshold. The third determination unit 2113 may determine whether the standard deviation exceeds a threshold. Alternatively, the third determining unit 2113 may determine whether a process capability index is below a threshold.

When the third determination unit 2113 determines that the variability exceeds the standard, the third determination unit 2113 evaluates that the quality of sleep is poor (S2509). When the third determination unit 2113 determines that the variability does not exceed the standard, the third determination unit 2113 evaluates that the quality of sleep is good (S2511).

The output processor 409 outputs an evaluation result in S2509 or S2511 (S2513). Specifically, the output processor 409 displays the evaluation result on the display device 455 as a comment. Then, the evaluation process (C) ends.

According to a seventh embodiment, it is possible to evaluate the quality of sleep focusing on stability of a midpoint time of a sleep period.

Eighth Embodiment

According to an eighth embodiment, a description is given of an example of evaluating the quality of sleep by statistically analyzing a midpoint time of a stay-in-bed period.

Figure 26:
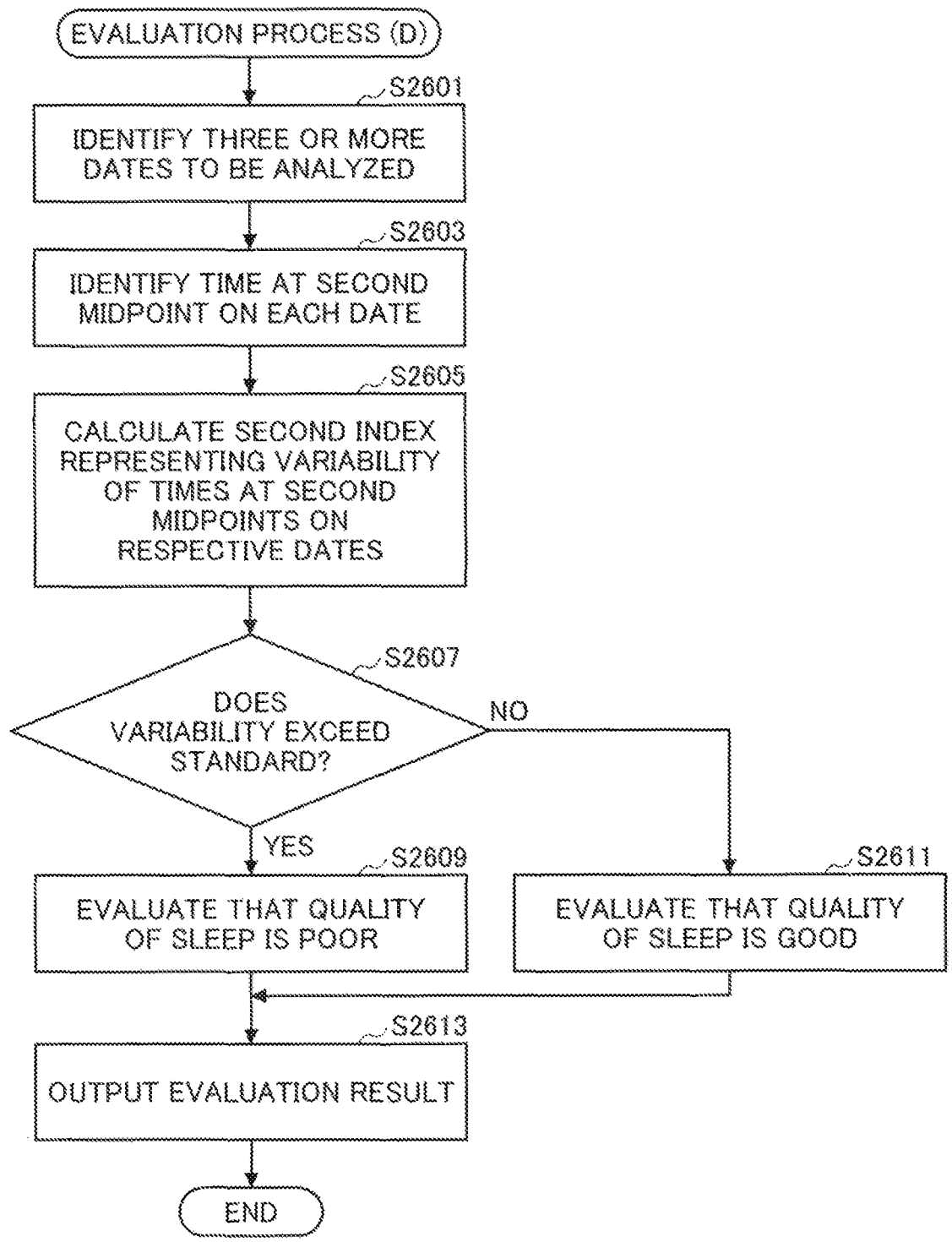
FIG. 26 is a diagram illustrating a flowchart of an evaluation process (D)

In the eighth embodiment, an evaluation process (D) is executed. FIG. 26 illustrates a flowchart of the evaluation process (D). The fourth identifier 2101, as in the case of S2501 illustrated in FIG. 25, identifies three or more dates to be analyzed (S2601).

The sixth calculator 2115 identifies a time at the second midpoint on each date (S2603). Then, the sixth calculator 2115 calculates a second index representing a variability of the times at the respective second midpoints (S2605). The second index is, for example, the variance or standard deviation. Alternatively, a process capability index may be used instead of the variance or standard deviation.

The fourth determination unit 2117 determines whether the variability exceeds a standard (S2607). The fourth determination unit 2117 determines, for example, whether the variance exceeds a threshold. The fourth determination unit 2117 may determine whether the standard deviation exceeds a threshold. Alternatively, the fourth determining unit 2117 may determine whether a process capability index is below a threshold.

When the fourth determination unit 2117 determines that the variability exceeds the standard, the fourth determination unit 2117 evaluates that the quality of sleep is poor (S2609). When the fourth determination unit 2117 determines that the variability does not exceed the standard, the fourth determination unit 2117 evaluates that the quality of sleep is good (S2611).

The output processor 409 outputs an evaluation result in S2609 or S2611 (S2613). Specifically, the output processor 409 displays the evaluation result on the display device 455 as a comment. Then, the evaluation process (D) ends.

According to the eighth embodiment, it is possible to evaluate the quality of sleep focusing on stability of a midpoint time of a stay-in-bed period.

Ninth Embodiment

According to a ninth embodiment, a description is given of an example of evaluating the quality of sleep by statistically analyzing a time difference (first time difference), where the time difference (first time difference) is obtained by subtracting the time at the first midpoint on the second day from the time at the first midpoint on the first day.

Figure 27:
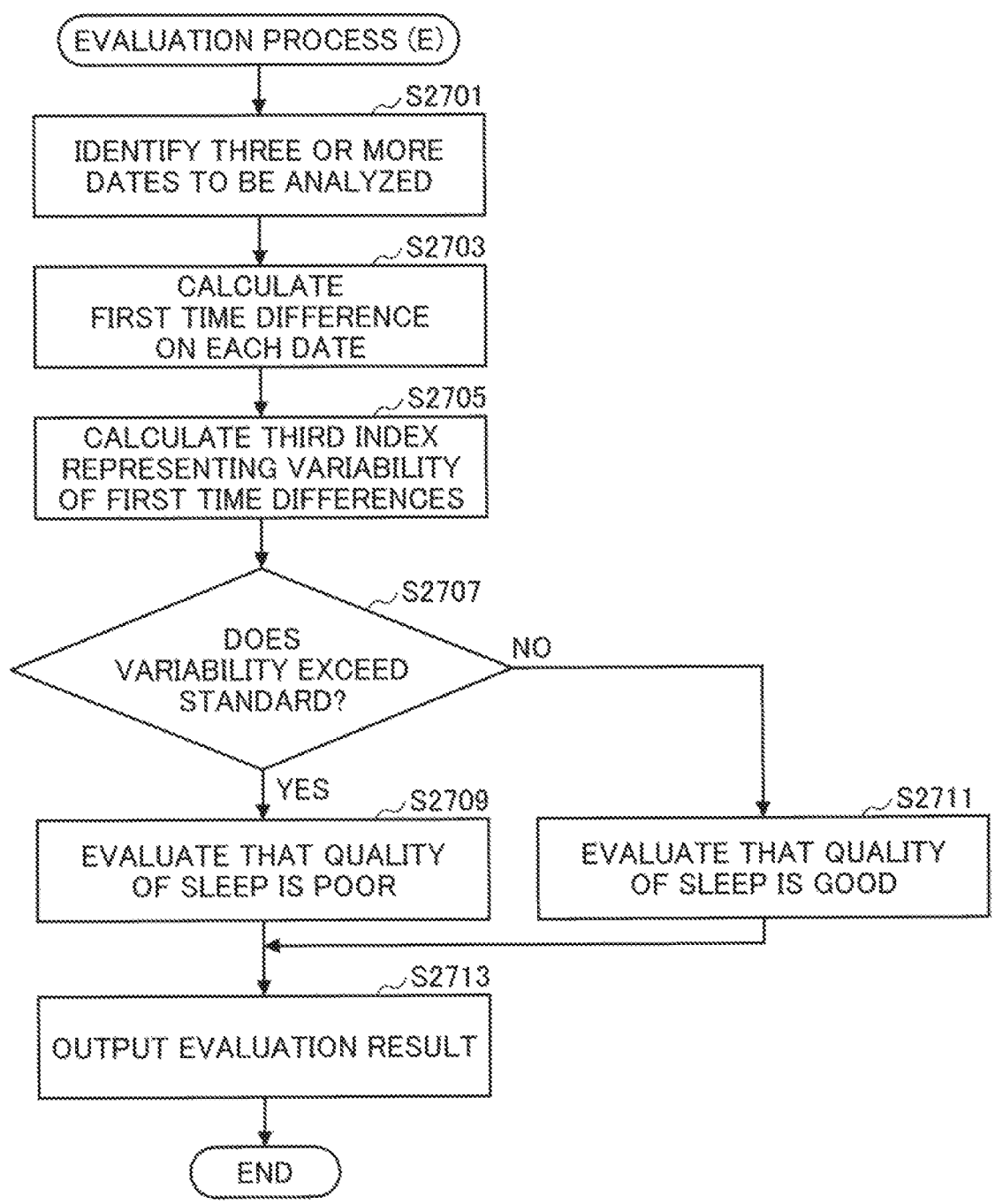
FIG. 27 is a diagram illustrating a flowchart of an evaluation process (E)

In the ninth embodiment, an evaluation process (E) is executed. FIG. 27 illustrates a flowchart of the evaluation process (E). The fourth identifier 2101, as in the case of S2501 illustrated in FIG. 25, identifies three or more dates to be analyzed (S2701).

The seventh calculator 2119 identifies a first time difference on each date (S2703). Specifically, the first time difference is obtained by subtracting, from a time at a first midpoint on a current date, a time at a first midpoint on an immediately preceding date selected from among the preceding dates identified in S2701.

Then, the seventh calculator 2119 calculates a third index representing a variability of the respective first time differences (S2705). The third index is, for example, the variance or standard deviation. Alternatively, a process capability index may be used instead of the variance or standard deviation.

The fifth determination unit 2121 determines whether the variability exceeds a standard (S2707). The fifth determination unit 2121 determines, for example, whether the variance exceeds a threshold. The fifth determination unit 2121 may determine whether the standard deviation exceeds a threshold. Alternatively, the fifth determining unit 2121 may determine whether a process capability index is below a threshold.

When the fifth determination unit 2121 determines that the variability exceeds the standard, the fifth determination unit 2121 evaluates that the quality of sleep is poor (S2709). When the fifth determination unit 2121 determines that the variability does not exceed the standard, the fifth determination unit 2121 evaluates that the quality of sleep is good (S2711).

The output processor 409 outputs an evaluation result in S2709 or S2711 (S2713). Specifically, the output processor 409 displays the evaluation result on the display device 455 as a comment.

Then, the evaluation process (E) ends.

According to the ninth embodiment, it is possible to evaluate the quality of sleep focusing on stability of a midpoint time of a sleep period.

Tenth Embodiment

According to a tenth embodiment, a description is given of an example of evaluating the quality of sleep by statistically analyzing a time difference (second time difference), where the time difference (second time difference) is obtained by subtracting the time at the second midpoint on the second day from the time at the second midpoint on the first day.

Figure 28:
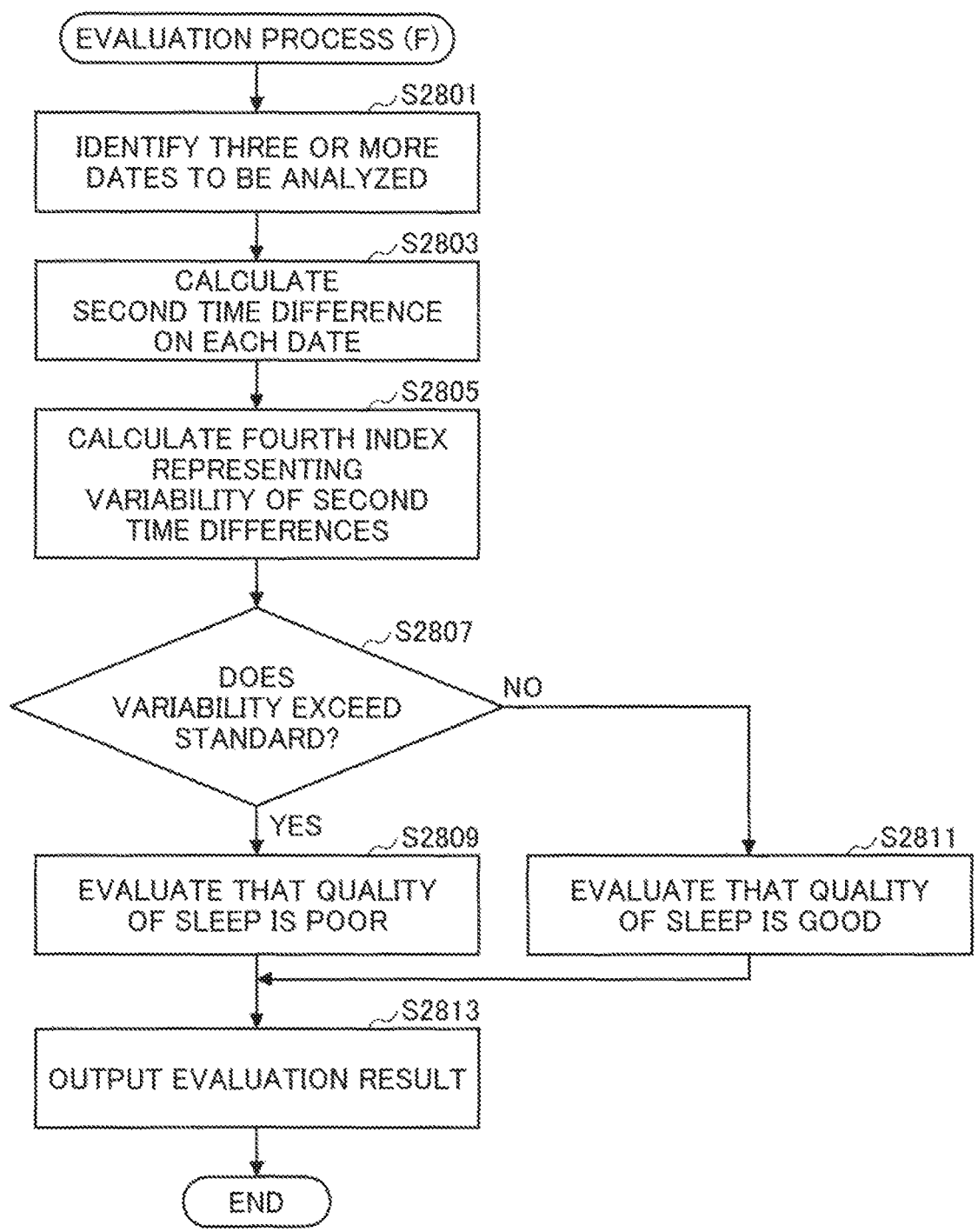
FIG. 28 is a diagram illustrating a flowchart of an evaluation process (F)

In the tenth embodiment, an evaluation process (F) is executed. FIG. 28 illustrates a flowchart of the evaluation process (F). The fourth identifier 2101, as in the case of S2501 illustrated in FIG. 25, identifies three or more dates to be analyzed (S2801).

The eighth calculator 2123 identifies a second time difference on each date (S2803). Specifically, the second time difference is obtained by subtracting, from a time at a second midpoint on a current date, a time at a second midpoint on an immediately preceding date selected from among the preceding dates identified in S2801.

Then, the eighth calculator 2123 calculates a fourth index representing a variability of the respective second time differences (S2805). The fourth index is, for example, the variance or standard deviation. Alternatively, a process capability index may be used instead of the variance or standard deviation.

The sixth determination unit 2125 determines whether the variability exceeds a standard (S2807).
The sixth determination unit 2125 determines, for example, whether the variance exceeds a threshold.
The sixth determination unit 2125 may determine whether the standard deviation exceeds a threshold.
Alternatively, the sixth determining unit 2125 may determine whether a process capability index is below a threshold.

When the sixth determination unit 2125 determines that the variability exceeds the standard, the sixth determination unit 2125 evaluates that the quality of sleep is poor (S2809). When the sixth determination unit 2125 determines that the variability does not exceed the standard, the sixth determination unit 2125 evaluates that the quality of sleep is good (S2811).

The output processor 409 outputs an evaluation result in S2809 or S2811 (S2813).
Specifically, the output processor 409 displays the evaluation result on the display device 455 as a comment.
Then, the evaluation process (F) ends.

According to the tenth embodiment, it is possible to evaluate the quality of sleep focusing on stability of a midpoint time of a stay-in-bed period.

Eleventh Embodiment

According to an eleventh embodiment, a description is given of an example of evaluating the quality of sleep based on a time difference (third time difference) between a time at a second midpoint and a time at a first midpoint.

Figure 29:
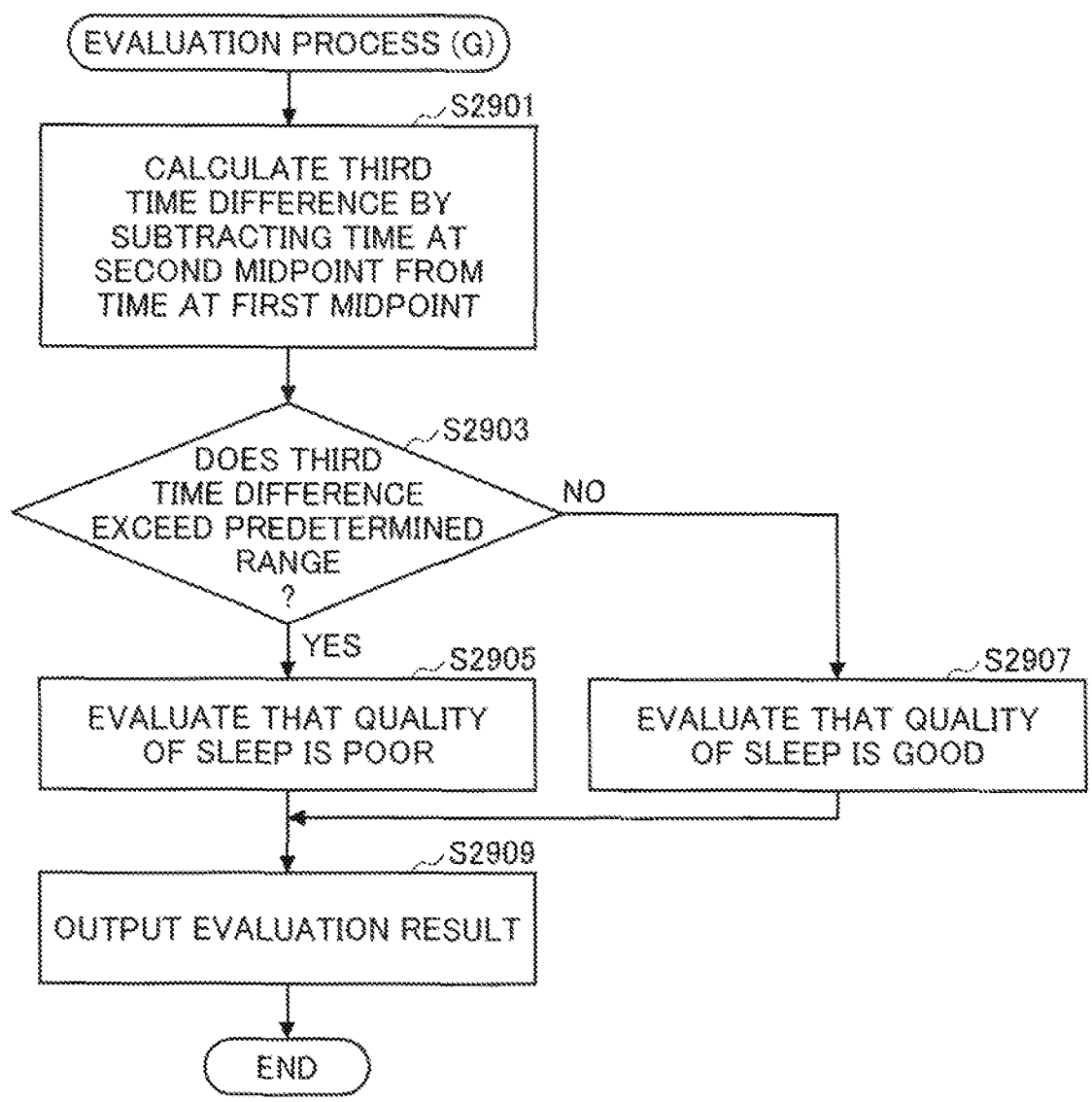
FIG. 29 is a diagram illustrating a flowchart of an evaluation process (G)

In the eleventh embodiment, an evaluation process (G) is executed. FIG. 29 illustrates a flowchart of the evaluation process (G). The ninth calculator 2127 calculates a third time difference by subtracting a time at the second midpoint on a current date from a time at the first midpoint on the current date (S2901).

The seventh determination unit 2129 determines whether the third time difference exceeds a predetermined range (S2903). The predetermined range is identified by lower and upper limits. The predetermined range may be identified by a lower limit without an upper limit. The predetermined range may be identified by an upper limit without a lower limit.

When the seventh determination unit 2129 determines that the third time difference exceeds the predetermined range, the seventh determination unit 2129 evaluates that the quality of sleep is poor (S2905). When the seventh determination unit 2129 determines that the third time difference does not exceed the predetermined range, the seventh determination unit 2129 evaluates that the quality of sleep is good (S2907).

The output processor 409 outputs an evaluation result in S2905 or S2907 (S2909). Specifically, the output processor 409 displays the evaluation result on the display device 455 as a comment. Then, the evaluation process (G) ends.

The evaluation process (G) may be applied to a date other than the current date. For example, the date to which the evaluation process (G) is applied may be received according to an instruction from a user of the information processing apparatus 201.

According to the eleventh embodiment, it is possible to evaluate the quality of sleep focusing on a method for sleeping during a stay-in-bed period.

Twelfth Embodiment

According to a twelfth embodiment, a description is given of an example of evaluating the quality of sleep by statistically analyzing the third time difference.

Figure 30:
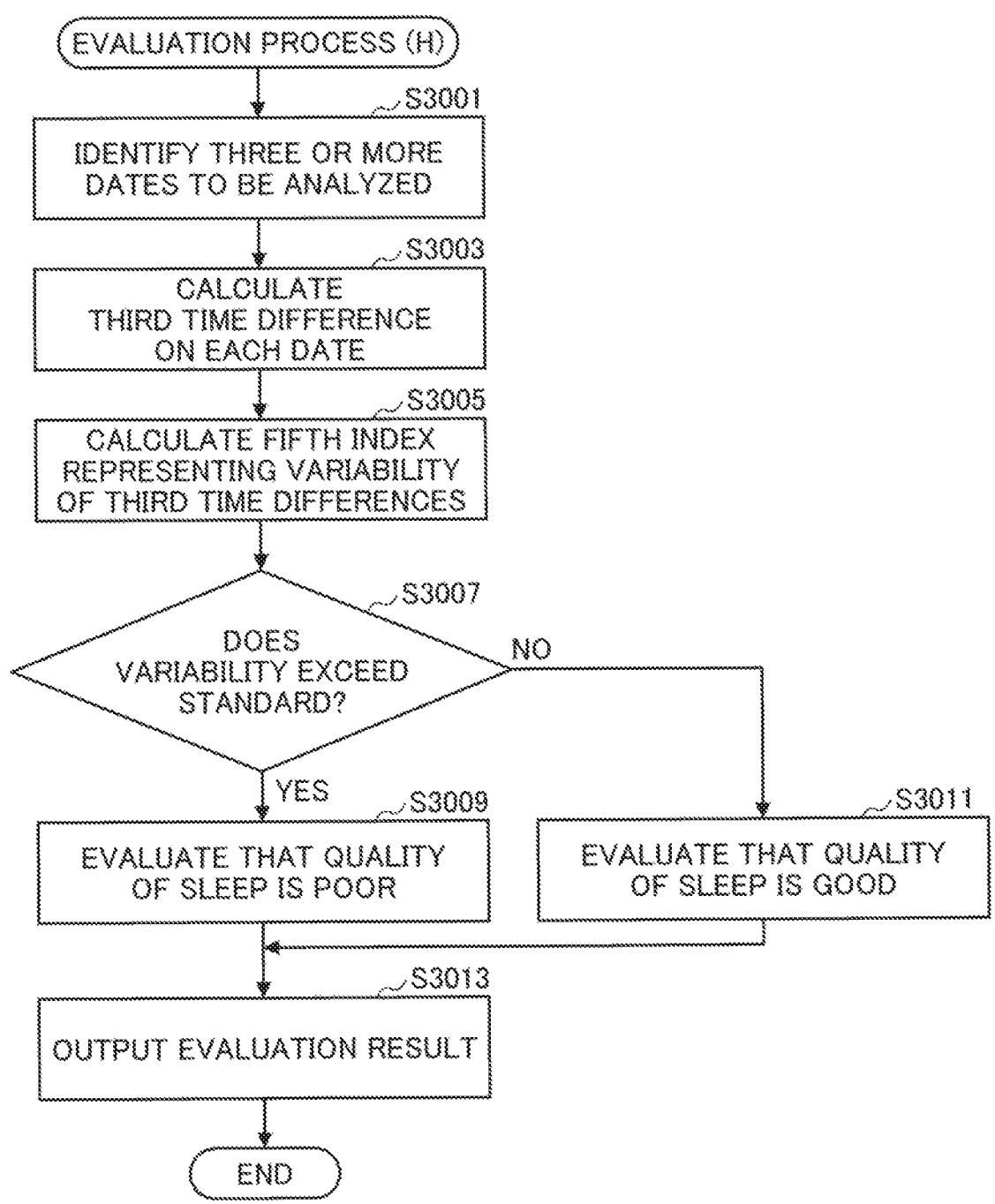
FIG. 30 is a diagram illustrating a flowchart of an evaluation process (H)

In the twelfth embodiment, an evaluation process (H) is executed.
FIG. 30 illustrates a flowchart of the evaluation process (H). The fourth identifier 2101, as in the case of S2501 illustrated in FIG. 25, identifies three or more dates to be analyzed (S3001).

The tenth calculator 2131 calculates a third time difference on each date (S3003).
Then, the tenth calculator 2131 calculates a fifth index representing a variability of the respective third time differences (S3005).
The fifth index is, for example, the variance or standard deviation.
Alternatively, a process capability index may be used instead of the variance or standard deviation.

The eighth determination unit 2133 determines whether the variability exceeds a standard (S3007).
The eighth determination unit 2133 determines, for example, whether the variance exceeds a threshold.
The eighth determination unit 2133 may determine whether the standard deviation exceeds a threshold.
Alternatively, the eighth determination unit 2133 may determine whether a process capability index is below a threshold.

When the eighth determination unit 2133 determines that the variability exceeds the standard, the eighth determination unit 2133 evaluates that the quality of sleep is poor (S3009). When the eighth determination unit 2133 determines that the variability does not exceed the standard, the eighth determination unit 2133 evaluates that the quality of sleep is good (S3011).

The output processor 409 outputs an evaluation result in S3009 or S3011 (S3013). Specifically, the output processor 409 displays the evaluation result on the display device 455 as a comment. Then, the evaluation process (H) ends.

According to the eleventh embodiment, it is possible to evaluate the quality of sleep focusing on a method for sleeping during a stay-in-bed period.

Thirteenth Embodiment

In thirteenth to fifteenth embodiments, examples of presenting various recommendation times are described. In the thirteenth to fifteenth embodiments, a description is given of an example of presenting a recommendation time (hereinafter referred to as a first recommendation time) recommended as a midpoint time of a sleep period.

Figure 31:
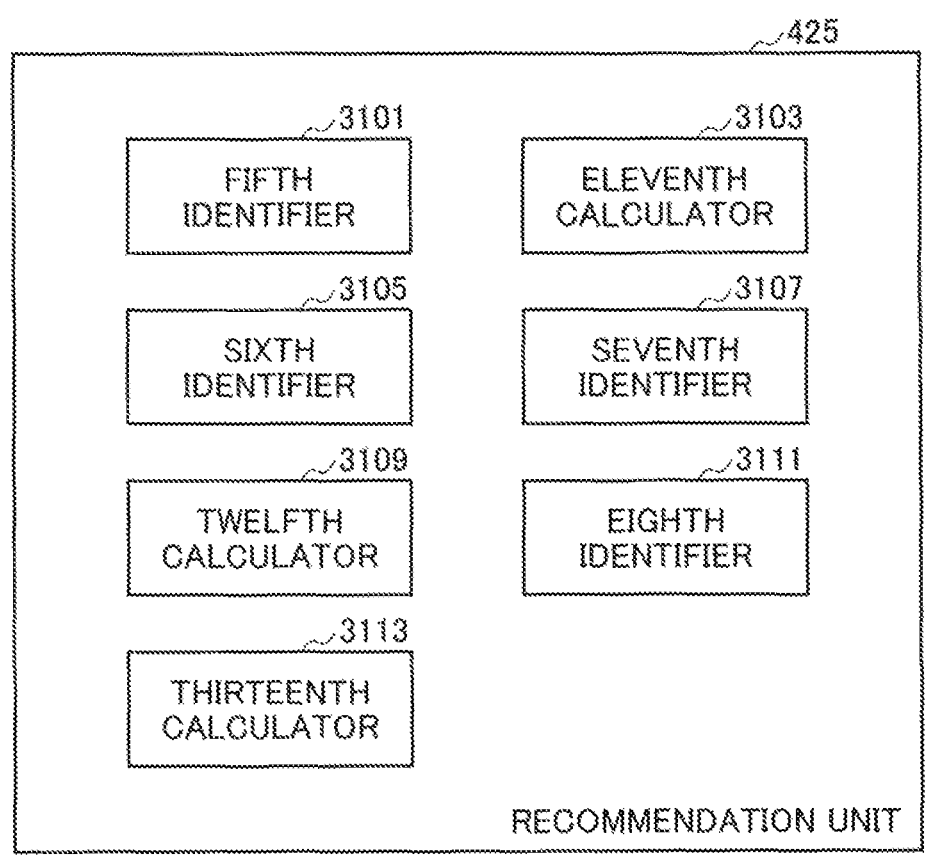
FIG. 31 is a diagram illustrating an example of a module configuration of a recommendation unit.

FIG. 31 illustrates an example of a module configuration of a recommendation unit 425 according to thirteenth to fifteenth embodiments. The recommendation unit 425 includes a fifth identifier 3101, an eleventh calculator 3103, a sixth identifier 3105, a seventh identifier 3107, a twelfth calculator 3109, an eighth identifier 3111, and a thirteenth calculator 3113.

In the thirteenth embodiment, the fifth identifier 3101 identifies dates to be analyzed. The eleventh calculator 3103 calculates the mean of times at the respective first midpoints.

In the fourteenth embodiment, the sixth identifier 3105 identifies a time (time point) recommended as a midpoint time of a sleep period. The seventh identifier 3107 identifies a standard sleep period. The twelfth calculator 3109 calculates a recommended sleep onset time (time point).

In the fifteenth embodiment, the eighth identifier 3111 identifies a standard time (time interval) required for falling asleep. The thirteenth calculator 3113 calculates a recommended time (time point) of getting into bed.

The fifth identifier 3101, the eleventh calculator 3103, the sixth identifier 3105, the seventh identifier 3107, the twelfth calculator 3109, the eighth identifier 3111, and the thirteenth calculator 3113 described above are implemented using hardware resources (e.g., FIG. 35) and a program that causes processors to execute a process described below.

The following illustrates a description of a recommendation process.
For example, a recommendation process is activated upon a user assigning a recommendation instruction to the information processing apparatus 201.
However, the recommendation process is activated at any desired time.
The main process may be followed by an automatic activation of the recommendation process.
The same applies to a recommendation process in other embodiments.
In addition, the recommendation processes may be interlinked.
Alternatively, the evaluation process may be interlinked with the recommendation process.

Figure 32:
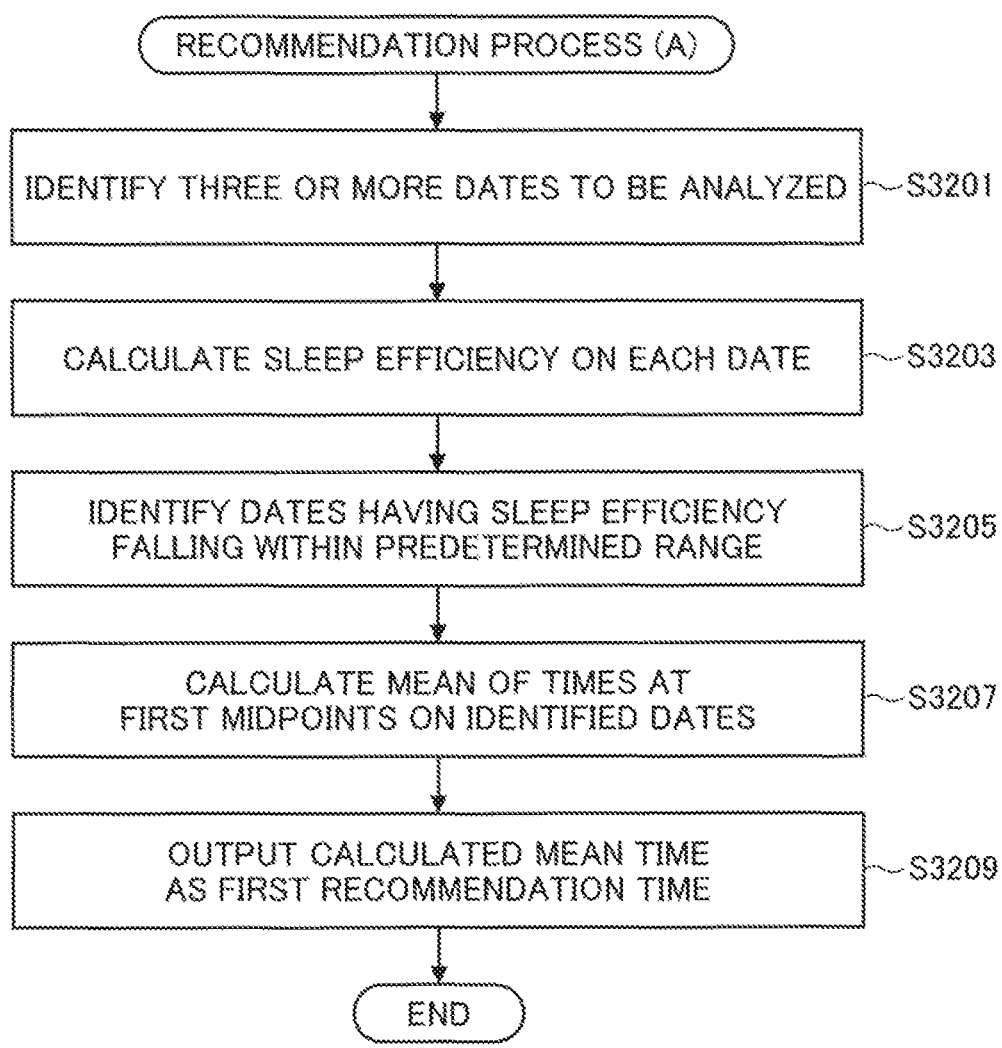
FIG. 32 is a diagram illustrating a flowchart of a recommendation process (A)

In this embodiment, a recommendation process (A) is executed. FIG. 32 illustrates a flowchart of a recommendation process (A). The fifth identifier 3101 identifies three or more dates to be analyzed (S3201). For example, the fifth identifier 3101 identifies dates of a current day and two preceding days. The three or more dates may be either continuous or discontinuous. The fifth identifier 3101 may execute a date identification process illustrated in FIG. 13.

The fifth identifier 3101 calculates sleep efficiency on each date (S3203). Sleep efficiency is a value obtained by dividing the length of a sleep period by the length of a stay-in-bed period.

The fifth identifier 3101 identifies a date having sleep efficiency that falls within a predetermined range (S3205). For example, the predetermined range may have a lower limit of 0.80 and an upper limit of 0.90.
That is, a date relating to sleep efficiency, which is 0.80 or more and 0.90 or less, is identified.
However, the predetermined range is not limited to this example.
The predetermined range may be identified by a lower limit without an upper limit.
The predetermined range may be identified by an upper limit without a lower limit.

The eleventh calculator 3103 calculates the mean of times at the respective first midpoints on the identified dates (S3207). For example, when three dates are identified, the eleventh calculator 3103 calculates the mean of three times at the first midpoints on the three identified dates.

The output processor 409 outputs the calculated mean time as a first recommendation time (S3209). Specifically, the output processor 409 displays, on the display unit 455, a comment indicating that the first recommendation time is recommended as the midpoint time of the sleep period. Then, the recommendation process (A) ends.

Note that the output form of the recommendation content is not limited to display.

The output processor 409 may print recommendation content. The output processor 409 may write recommendation content to a storage medium. Alternatively, the output processor 409 may transmit recommendation content. The same applies to a recommendation process illustrated below.

According to the present embodiment, a desired midpoint time of a sleep period may be obtained for improving the quality of sleep.

Fourteenth Embodiment

According to the fourteenth embodiment, a description is given of an example of presenting a recommendation time (hereinafter referred to as a second recommendation time) recommended as a sleep onset time.

Figure 33:
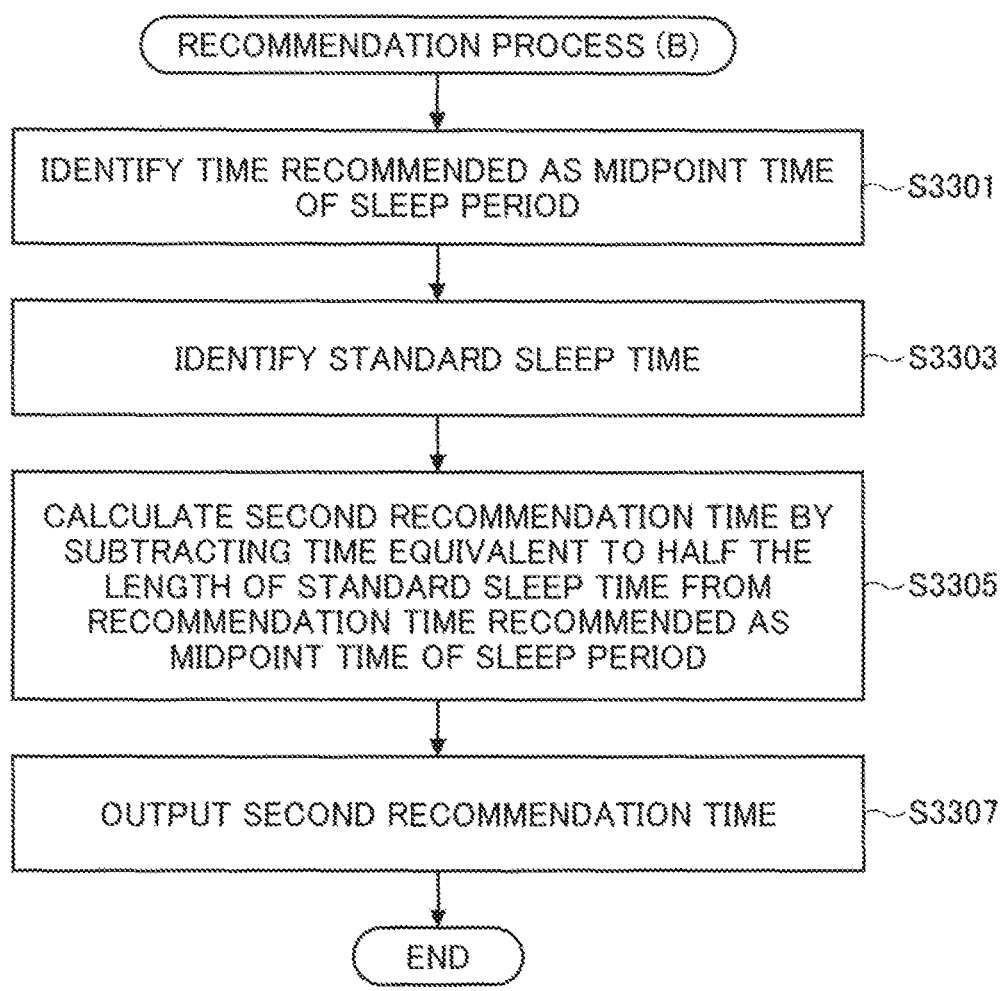
FIG. 33 is a diagram illustrating a flowchart of a recommendation process (B)

In the fourteenth embodiment, a recommendation process (B) is executed.
FIG. 33 illustrates a flowchart of the recommendation process (B).
The sixth identifier 3105 identifies a time recommended as a midpoint time of the sleep period (S3301).
For example, a first recommendation time determined by the recommendation process (A) may be used as the recommendation time.
Alternatively, a time recommended as the midpoint time of the sleep period may be received according to an instruction from a user of the information processing apparatus 201.

The seventh identifier 3107 identifies a standard sleep period (S3303).
For example, in the recommendation process (A), the standard sleep period may be the mean of sleep periods on the dates to be analyzed.
Alternatively, the standard sleep period may be received according to an instruction from a user of the information processing apparatus 201.

The twelfth calculator 3109 calculates a second recommendation time (time point) by subtracting a time (time interval) equivalent to half the length of the standard sleep period from the recommendation time (time point) recommended as the midpoint time of the sleep period (S3305).

The output processor 409 then outputs a second recommendation time (S3307). Specifically, the output processor 409 displays, on the display unit 455, a comment indicating that the second recommendation time is recommended as a sleep onset time. Then, the recommendation process (B) ends.

According to the fourteenth embodiment, a desired sleep onset time of sleep may be obtained for improving the quality.

Fifteenth Embodiment

According to the fifteenth embodiment, a description is given of an example of presenting a recommendation time (hereinafter referred to as a third recommendation time) recommended as a time of getting into bed.

Figure 34:
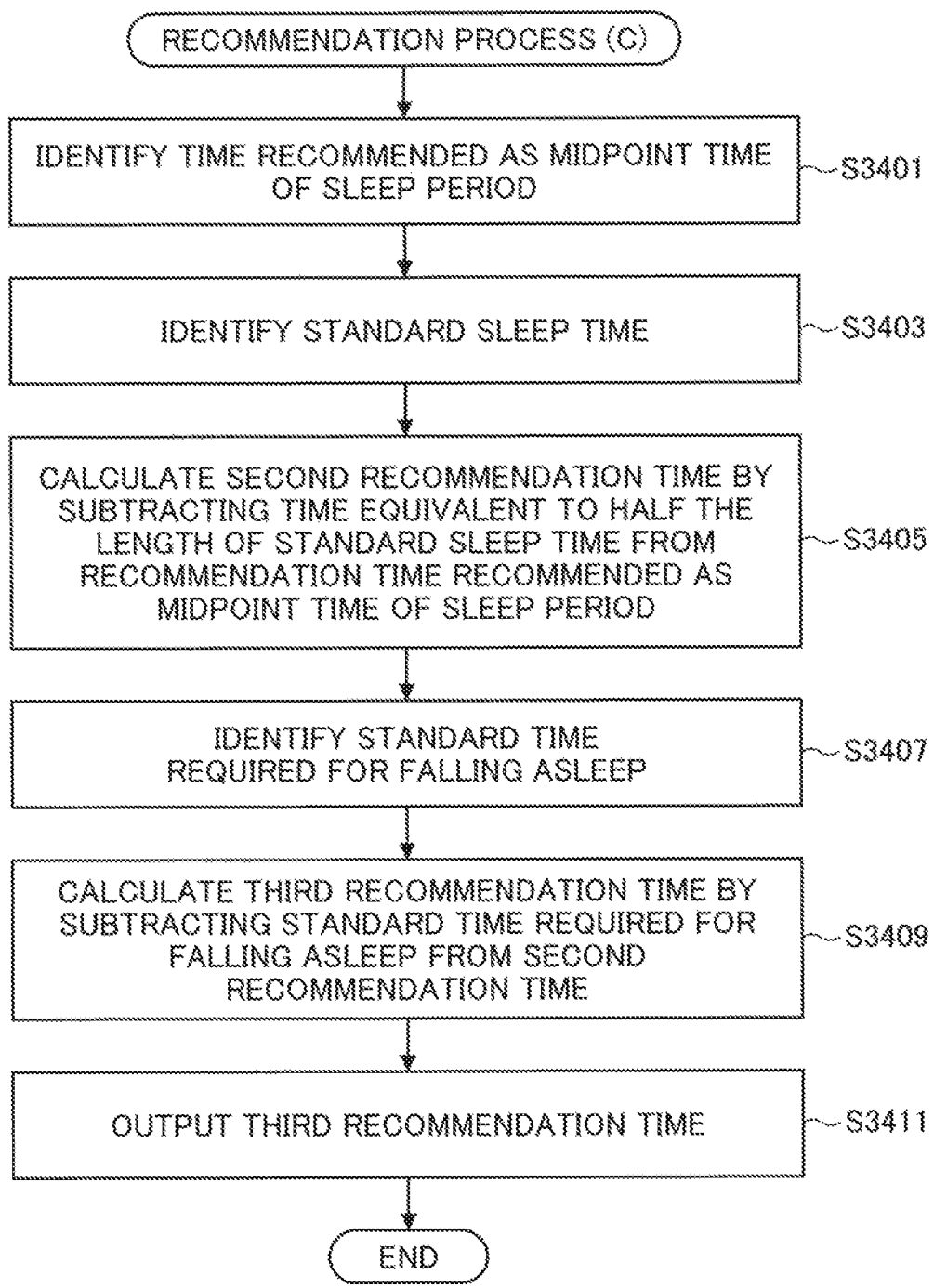
FIG. 34 is a diagram illustrating a flowchart of a recommendation process (C)

In the fifteenth embodiment, a recommendation process (C) is executed. FIG. 34 illustrates a flowchart of the recommendation process (C). Steps S3401 to S3405 are similar to steps S3301 to S3305 illustrated in FIG. 33.

The eighth identifier 3111 identifies a standard time required for falling asleep (S3407). For example, the standard time required for falling asleep may be the mean of times required for falling asleep on the dates to be analyzed in the recommendation process (A). The time required for falling asleep may be calculated by subtracting a time of getting into bed from a sleep onset time. Alternatively, the standard time required for falling asleep may be received according to an instruction from a user of the information processing apparatus 201.

The thirteenth calculator 3113 calculates a third recommendation time by subtracting the standard time required for falling asleep from the second recommendation time (S3409).

The output processor 409 then outputs the third recommendation time (S3411). Specifically, the output processor 409 displays, on the display unit 455, a comment indicating that the third recommendation time is recommended as a time of getting into bed. Then, the recommendation process (C) ends.

According to the present embodiment, a desired time of getting into bed may be obtained for improving the quality of sleep.

Although the embodiments of the present invention have been described above, the present invention is not limited thereto. For example, the above functional block configuration may not match the program module configuration.

In addition, the configuration of each storage area described above may be exemplary, and storage areas may not be required to have the above-described configuration. Further, in the flowcharts, unless the processing results change, the order of processes may be changed or multiple processes may be executed in parallel.

The above-described information processing apparatus 201 and the user terminal 203 are a computer device as illustrated in FIG. 35, in which the memory 2501, the CPU (Central Processing Unit) 2503, the HDD (hard disk drive) 2505, the display controller 2507 connected to the display device 2509, the drive device 2513 for the removable disk 2511, the input device 2515, and the communication controller 2517 for connecting to a network are connected via the bus 2519.

The operating system (OS) and application programs for executing a process in the embodiments are stored in the HDD 2505 and loaded from the HDD 2505 onto the memory 2501 when executed by CPU 2503.

The CPU 2503 controls the display controller 2507, the communication controller 2517, and the drive device 2513 according to descriptions of the application programs to perform predetermined operations.

The data being processed is mainly stored in the memory 2501, but may be stored in the HDD 2505.

In the embodiments of the present invention, the application programs for performing processes described above may be stored and distributed on a computer readable removable disk 2511, which may be installed on an HDD 2505 from a drive device 2513.

The application programs may be installed in the HDD 2505 via a network such as the Internet and the communication controller 2517.

Such a computer device implements various functions described above by mutually associating hardware such as the CPU 2503, and the memory 2501 with programs such as the OS and application programs in a complex fashion.

The embodiments of the present invention described above are summarized as follows.

The information processing method according to the present embodiment includes (A) identifying a sleep onset time and an awakening time based on time series data relating to an activity status of a user;

(B) calculating a first midpoint at which an interval between the sleep onset time and the awakening time is evenly divided into two; and (C) outputting information indicating a time at the calculated first midpoint.

According to such a configuration, it is easy to identify the midpoint time of the sleep period. In the example described above, the step (A) is performed by the first identifier 405. The step (B) is performed by the first calculator 407. The step (C) is performed by the output processor 409.

Further, in the step (C) of outputting the information, a first display element representing a position of the first midpoint may be added to a graph representing the sleep period. In addition, the graph to which the first display element is added may be displayed.

According to such a configuration, it is easier to visually identify the midpoint time of the sleep period.

In addition, the information processing method may further include repeating a following process for each of a plurality of days. The following process includes identifying the sleep onset time and the awakening time based on the time series data;

calculating a first midpoint at which an interval between the sleep onset time and the awakening time is evenly divided into two;

adding a first display element indicating a position of the first midpoint in a graph representing a sleep period; and displaying the graph to which the first display element is added.

According to such a configuration, it is easier to visually identify stability of the midpoint time of the sleep period.

In addition, the information processing method may further include identifying a time of getting into bed and a time of getting out of bed, and calculating a second midpoint at which an interval between the time of getting into bed and the time of getting out of bed is evenly divided into two. Moreover, the outputting information may further include adding a first display element indicating a position of a first midpoint and a second display element indicating a position of the second midpoint to a graph representing the sleep period, and displaying the graph to which the first display element and the second display element are added.

According to such a configuration, it is easier to visually identify the midpoint time of a stay-in-bed period. It is also easier to identify an interrelationship between the midpoint time of the sleep period and the midpoint time of the stay-in-bed period.

Further, the information processing method according to the present embodiment may include repeating a first process and a second process, for each of a plurality of days, wherein the first process includes identifying the sleep onset time and the awakening time based on the time series data;

calculating a first midpoint at which an interval between the sleep onset time and the awakening time is evenly divided into two;

adding a first display element indicating a position of the first midpoint to a graph representing a sleep period, and wherein the second process includes identifying a time of getting into bed and a time of getting out of bed based on the time series data;

calculating a second midpoint at which an interval between the time of getting into bed and the time of getting out of bed is evenly divided into two; and adding a second display element indicating a position of the second midpoint to the graph; and displaying the graph to which the first display element and the second display element are added.

According to such a configuration, it is easier to visually identify stability of the midpoint time of the stay-in-bed period.

Further, the information processing method according to the present embodiment may further include calculating a time difference between times of the first midpoints in two or more sleep periods; and determining a quality of sleep based on the calculated time difference.

According to such a configuration, it is possible to evaluate the quality of sleep focusing on stability of a midpoint time of a sleep period.

Further, the information processing method according to the present embodiment may further include calculating an index representing a variability of times at the respective first midpoints in two or more sleep periods; and determining a quality of sleep based on the calculated index.

According to such a configuration, it is possible to evaluate the quality of sleep focusing on stability of a midpoint time of a sleep period.

Further, the information processing method according to the present embodiment may further include identifying two or more sleep periods for which a sleep efficiency meeting a predetermined standard is obtained; and calculating a mean of times at respective first midpoints in the identified two or more sleep periods.

According to such a configuration, a desired midpoint time of a sleep period may be obtained for improving the quality of sleep.

Further, the information processing method according to the present embodiment may further include identifying a first time recommended as a midpoint time of a sleep period, based on a time at the first midpoint of one or more sleep periods; and calculating a second time recommended as a time of getting into bed or recommended as a sleep onset time, based on the first recommendation time.

According to such a configuration, a desired sleep onset time may be obtained for improving the quality of sleep.

Further, the information processing method according to the present embodiment may further include identifying dates according to a distinction between holiday and working day or according to a same type of working arrangement, as dates corresponding to two or more sleep periods.

According to such a configuration, sleep periods on different working conditions may be excluded from a processing target.

According to one aspect of embodiments, it is possible to output the midpoint time of a sleep period.

It should be noted that a program may be created for causing a computer to perform processing by the above-described method, and the program may be stored in a computer-readable storage medium or storage device such as, for example, a flexible disk, a CD-ROM, an optical magnetic disk, semiconductor memory, a hard disk, or the like. Typical intermediate processing results are temporarily stored in storage devices such as main memory.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present inventions have been described in detail, it should be understood that the various changes, substitutions, and alterations could be made hereto without departing from the spirit and scope of the invention.

What is claimed is:

1. An information processing method executed by a computer, the information processing method comprising:
    identifying a sleep onset time and an awakening time based on time series data relating to an activity status of a user;
    calculating a first midpoint at which an interval between the sleep onset time and the awakening time is evenly divided into two;
    outputting information indicating a time at the calculated first midpoint;
    identifying a time of getting into bed and a time of getting out of bed based on the time series data; and
    calculating a second midpoint at which an interval between the time of getting into bed and the time of getting out of bed is evenly divided into two,
    wherein the outputting information includes
        adding to a graph representing a sleep period a first display element indicating a position of the first midpoint and a second display element indicating a position of the second midpoint; and
        displaying the graph to which the first display element and the second display element are added.

2. The information processing method as claimed in claim 1, further comprising
    repeating a first process and a second process, for each of a plurality of days,
    wherein the first process includes
        identifying the sleep onset time and the awakening time based on the time series data;
        calculating the first midpoint at which an interval between the sleep onset time and the awakening time is evenly divided into two; and
        adding the first display element indicating a position of the first midpoint in the graph representing the sleep period, and
    wherein the second process includes
        identifying the time of getting into bed and the time of getting out of bed based on the time series data;
        calculating the second midpoint at which an interval between the time of getting into bed and the time of getting out of bed is evenly divided into two;
        adding the second display element indicating a position of the second midpoint in the graph; and
        displaying the graph to which the first display element and the second display element are added.

3. The information processing method as claimed in claim 1, further comprising
    calculating a time difference between times of the first midpoints in two or more sleep periods; and
    determining a quality of sleep based on the calculated time difference.

4. The information processing method as claimed in claim 3, further comprising
    identifying dates, as dates corresponding to the two or more sleep periods, according to a distinction between a holiday and a working day or according to a same type of working arrangement.

5. The information processing method as claimed in claim 1, further comprising
    calculating an index representing a variability of times at the respective first midpoints in two or more sleep periods; and determining a quality of sleep based on the calculated index.

6. The information processing method as claimed in claim 1, further comprising
identifying two or more sleep periods for which a sleep efficiency meeting a predetermined standard is obtained; and
calculating a mean of times at the respective first midpoints in the identified two or more sleep periods.

7. The information processing method as claimed in claim 1, further comprising
identifying a first time that is recommended as a midpoint time of a sleep period, based on a time at the first midpoint of one or more sleep periods; and
calculating a second time that is recommended as a time of getting into bed or recommended as a sleep onset time, based on the identified first time.

8. A non-transitory computer-readable recording medium having stored therein a program for causing a computer to execute a process comprising:
identifying a sleep onset time and an awakening time based on time series data relating to an activity status of a user;
calculating a first midpoint at which an interval between the sleep onset time and the awakening time is evenly divided into two;
outputting information indicating a time at the calculated first midpoint;
identifying a time of getting into bed and a time of getting out of bed based on the time series data; and
calculating a second midpoint at which an interval between the time of getting into bed and the time of getting out of bed is evenly divided into two,
wherein the outputting information includes
adding to a graph representing a sleep period a first display element indicating a position of the first midpoint and a second display element indicating a position of the second midpoint; and
displaying the graph to which the first display element and the second display element are added.

9. An information processing apparatus comprising:
a memory; and
one or more processors coupled to the memory and configured to
calculate a first midpoint at which an interval between a sleep onset time and an awakening time is evenly divided into two, the sleep onset time and the awakening time being identified based on time series data relating to an activity status of a user;
output information indicating a time at the calculated first midpoint;
identify a time of getting into bed and a time of getting out of bed based on the time series data; and
calculate a second midpoint at which an interval between the time of getting into bed and the time of getting out of bed is evenly divided into two,
wherein in outputting the information, the one or more processors are configured to
add to a graph representing a sleep period a first display element indicating a position of the first midpoint and a second display element indicating a position of the second midpoint; and
display the graph to which the first display element and the second display element are added.

* * * * *